(12) United States Patent
Ivosevic et al.

(10) Patent No.: US 11,298,061 B2
(45) Date of Patent: Apr. 12, 2022

(54) BLOOD SAMPLE MANAGEMENT USING OPEN CELL FOAM

(71) Applicant: Becton, Dickinson and Company, Franklin Lakes, NJ (US)

(72) Inventors: Milan Ivosevic, Kinnelon, NJ (US); Alexander James Blake, Ridgewood, NJ (US); Ryan W. Muthard, Wynnewood, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 271 days.

(21) Appl. No.: 14/861,167

(22) Filed: Sep. 22, 2015

(65) Prior Publication Data

US 2016/0103046 A1    Apr. 14, 2016

Related U.S. Application Data

(60) Provisional application No. 62/063,536, filed on Oct. 14, 2014, provisional application No. 62/207,618, filed on Aug. 20, 2015.

(51) Int. Cl.
*B01L 3/00* (2006.01)
*A61B 5/15* (2006.01)
(Continued)

(52) U.S. Cl.
CPC ........ *A61B 5/150755* (2013.01); *A61B 5/151* (2013.01); *A61B 5/150022* (2013.01);
(Continued)

(58) Field of Classification Search
CPC .......... A61B 10/0045; A61B 5/150022; A61B 5/150221; A61B 5/150236; A61B 5/150244; A61B 5/150259; A61B 5/150305; A61B 5/150343; A61B 5/150351; A61B 5/150366;
(Continued)

(56) References Cited

U.S. PATENT DOCUMENTS 3,626,929 A    12/1971  Sanz
3,819,913 A     6/1974  Carter et al.
(Continued)

FOREIGN PATENT DOCUMENTS

CN       1365987 A    8/2002
CN     101036591 A    9/2007
(Continued)

*Primary Examiner* — Samuel P Siefke
(74) *Attorney, Agent, or Firm* — The Webb Law Firm

(57) ABSTRACT

A specimen mixing and transfer device adapted to receive a sample is disclosed. The specimen mixing and transfer device includes a housing, a material including pores that is disposed within the housing, and a dry anticoagulant powder within the pores of the material. In one embodiment, the material is a sponge material. In other embodiments, the material is an open cell foam. In one embodiment, the material is treated with an anticoagulant to form a dry anticoagulant powder finely distributed throughout the pores of the material. A blood sample may be received within the specimen mixing and transfer device. The blood sample is exposed to and mixes with the anticoagulant powder while passing through the material.

13 Claims, 16 Drawing Sheets

(51) Int. Cl.
  *A61B 5/151* (2006.01)
  *G01N 1/36* (2006.01)
  *A61J 1/06* (2006.01)
  *A61J 1/14* (2006.01)
  *A61B 10/00* (2006.01)

(52) U.S. Cl.
  CPC ...... *A61B 5/15113* (2013.01); *A61B 5/15142* (2013.01); *A61B 5/150221* (2013.01); *A61B 5/150236* (2013.01); *A61B 5/150244* (2013.01); *A61B 5/150259* (2013.01); *A61B 5/150305* (2013.01); *A61B 5/150343* (2013.01); *A61B 5/150351* (2013.01); *A61B 5/150366* (2013.01); *A61J 1/067* (2013.01); *A61J 1/1412* (2013.01); *A61J 1/1475* (2013.01); *B01L 3/502* (2013.01); *B01L 3/502707* (2013.01); *B01L 3/502746* (2013.01); *B01L 3/567* (2013.01); *G01N 1/36* (2013.01); *A61B 10/0045* (2013.01); *B01L 2200/12* (2013.01); *B01L 2300/042* (2013.01); *B01L 2300/069* (2013.01); *B01L 2300/0838* (2013.01); *B01L 2300/0858* (2013.01); *B01L 2300/12* (2013.01); *B01L 2300/123* (2013.01); *B01L 2300/16* (2013.01); *B01L 2400/0478* (2013.01); *B01L 2400/06* (2013.01); *B01L 2400/08* (2013.01); *B01L 2400/086* (2013.01); *B01L 2400/088* (2013.01)

(58) Field of Classification Search
  CPC .............. A61B 5/150755; A61B 5/151; A61B 5/15113; A61B 5/15142; A61J 1/067; A61J 1/1412; A61J 1/1475; B01L 2200/12; B01L 2300/042; B01L 2300/069; B01L 2300/0838; B01L 2300/0858; B01L 2300/12; B01L 2300/123; B01L 2300/16; B01L 2400/0478; B01L 2400/06; B01L 2400/08; B01L 2400/086; B01L 2400/088; B01L 3/502; B01L 3/502707; B01L 3/502746; B01L 3/567; G01N 1/36
  See application file for complete search history.

(56) References Cited

U.S. PATENT DOCUMENTS

| | | | |
|---|---|---|---|
| 3,916,205 | A | 10/1975 | Kleinerman |
| 3,963,350 | A | 6/1976 | Watanabe et al. |
| 4,088,448 | A | 5/1978 | Lilja et al. |
| 4,125,828 | A | 11/1978 | Resnick et al. |
| 4,133,304 | A | 1/1979 | Bailey |
| 4,133,873 | A | 1/1979 | Noller |
| 4,337,222 | A | 6/1982 | Kitajima et al. |
| 4,501,496 | A | 2/1985 | Griffin |
| 4,703,761 | A | 11/1987 | Rathbone et al. |
| 4,727,020 | A | 2/1988 | Recktenwald |
| 4,751,188 | A | 6/1988 | Valet |
| 4,857,735 | A | 8/1989 | Noller |
| 4,959,305 | A | 9/1990 | Woodrum |
| 5,014,718 | A | 5/1991 | Mitchen |
| 5,053,626 | A | 10/1991 | Tillotson |
| 5,073,857 | A | 12/1991 | Peters et al. |
| 5,102,625 | A | 4/1992 | Milo |
| 5,134,662 | A | 7/1992 | Bacus et al. |
| 5,159,642 | A | 10/1992 | Kosaka |
| 5,187,749 | A | 2/1993 | Sugimoto et al. |
| 5,196,709 | A | 3/1993 | Berndt et al. |
| 5,200,152 | A | 4/1993 | Brown |
| 5,294,799 | A | 3/1994 | Aslund et al. |
| 5,332,905 | A | 7/1994 | Brooker et al. |
| 5,348,859 | A | 9/1994 | Brunhouse et al. |
| 5,385,539 | A | 1/1995 | Maynard |
| 5,489,771 | A | 2/1996 | Beach et al. |
| 5,491,343 | A | 2/1996 | Brooker |
| 5,528,045 | A | 6/1996 | Hoffman et al. |
| 5,547,849 | A | 8/1996 | Baer et al. |
| 5,556,764 | A | 9/1996 | Sizto et al. |
| 5,592,291 | A | 1/1997 | Iida |
| 5,599,668 | A | 2/1997 | Stimpson et al. |
| 5,627,037 | A | 5/1997 | Ward et al. |
| 5,661,558 | A | 8/1997 | Nogami et al. |
| 5,674,457 | A | 10/1997 | Williamsson et al. |
| 5,675,155 | A | 10/1997 | Pentoney, Jr. et al. |
| 5,681,529 | A | 10/1997 | Taguchi et al. |
| 5,692,503 | A | 12/1997 | Kuenstner |
| 5,732,150 | A | 3/1998 | Zhou et al. |
| 5,733,721 | A | 3/1998 | Hemstreet, III et al. |
| 5,770,158 | A | 6/1998 | Eischen et al. |
| 5,773,301 | A | 6/1998 | Ziegler |
| 5,851,835 | A | 12/1998 | Groner |
| 5,890,828 | A | 4/1999 | Gueret |
| 5,898,487 | A | 4/1999 | Hage |
| 5,933,233 | A | 8/1999 | Günther |
| 5,938,439 | A | 8/1999 | Mertins et al. |
| 6,043,880 | A | 3/2000 | Andrews et al. |
| 6,064,474 | A | 5/2000 | Lee et al. |
| 6,064,897 | A | 5/2000 | Lindberg et al. |
| 6,094,592 | A | 7/2000 | Yorkey et al. |
| 6,103,197 | A | 8/2000 | Werner |
| 6,154,282 | A | 11/2000 | Lilge et al. |
| 6,159,740 | A | 12/2000 | Hudson et al. |
| 6,181,418 | B1 | 1/2001 | Palumbo et al. |
| 6,187,592 | B1 | 2/2001 | Gourley |
| 6,214,629 | B1 | 4/2001 | Freitag et al. |
| 6,226,347 | B1 | 5/2001 | Golenhoffen |
| 6,262,798 | B1 | 7/2001 | Shepherd et al. |
| 6,294,094 | B1 | 9/2001 | Muller et al. |
| 6,305,804 | B1 | 10/2001 | Rice et al. |
| 6,342,376 | B1 | 1/2002 | Kozian et al. |
| 6,350,613 | B1 | 2/2002 | Wardlaw et al. |
| 6,410,341 | B1 | 6/2002 | Freitag et al. |
| 6,448,018 | B1 | 9/2002 | Nakayana et al. |
| 6,453,060 | B1 | 9/2002 | Riley et al. |
| 6,477,394 | B2 | 11/2002 | Rice et al. |
| 6,479,299 | B1 | 11/2002 | Parce et al. |
| 6,493,567 | B1 | 12/2002 | Krivitski et al. |
| 6,519,025 | B2 | 2/2003 | Shepherd et al. |
| 6,563,585 | B1 | 5/2003 | Rao et al. |
| 6,594,075 | B1 | 7/2003 | Kanao et al. |
| 6,611,320 | B1 | 8/2003 | Lindberg et al. |
| 6,612,111 | B1 | 9/2003 | Hodges et al. |
| 6,638,769 | B2 | 10/2003 | Lilja et al. |
| 6,665,060 | B1 | 12/2003 | Zahniser et al. |
| 6,696,240 | B1 | 2/2004 | Kloepfer et al. |
| 6,716,588 | B2 | 4/2004 | Sammak et al. |
| 6,723,290 | B1 | 4/2004 | Wardlaw |
| 6,740,527 | B1 | 5/2004 | Wong et al. |
| 6,825,921 | B1 | 11/2004 | Modlin et al. |
| 6,828,567 | B2 | 12/2004 | Amirkhanian et al. |
| 6,831,733 | B2 | 12/2004 | Pettersson et al. |
| 6,858,400 | B2 | 2/2005 | Bristow |
| 6,862,534 | B2 | 3/2005 | Sterling et al. |
| 6,869,405 | B2 | 3/2005 | Marsden |
| 6,869,570 | B2 | 3/2005 | Wardlaw |
| 6,898,458 | B2 | 5/2005 | Zeng et al. |
| 6,960,165 | B2 | 11/2005 | Ueno et al. |
| 6,985,224 | B2 | 1/2006 | Hart |
| 6,999,173 | B2 | 2/2006 | Kleinfeld et al. |
| 7,075,628 | B2 | 7/2006 | Shepherd et al. |
| 7,094,562 | B2 | 8/2006 | Bittner |
| 7,096,124 | B2 | 8/2006 | Sterling et al. |
| 7,115,841 | B2 | 10/2006 | Zeng et al. |
| 7,133,545 | B2 | 11/2006 | Douglass et al. |
| 7,139,073 | B1 | 11/2006 | Terada |
| 7,146,372 | B2 | 12/2006 | Bacus et al. |
| 7,149,332 | B2 | 12/2006 | Bacus et al. |
| 7,271,912 | B2 | 9/2007 | Sterling et al. |
| 7,279,134 | B2 | 10/2007 | Chan et al. |
| 7,303,922 | B2 | 12/2007 | Jeng et al. |
| 7,319,894 | B2 | 1/2008 | Higgins |

(56) References Cited

U.S. PATENT DOCUMENTS

| | | |
|---|---|---|
| 7,324,674 B2 | 1/2008 | Ozawa et al. |
| 7,378,054 B2 | 5/2008 | Karmali |
| 7,420,660 B2 | 9/2008 | Muller et al. |
| 7,426,407 B2 | 9/2008 | Higgins |
| 7,477,382 B2 | 1/2009 | Grey et al. |
| 7,500,569 B2 | 3/2009 | Manoussakis et al. |
| 7,515,268 B1 | 4/2009 | Ayliffe et al. |
| 7,518,727 B2 | 4/2009 | Pentoney, Jr. et al. |
| 7,539,335 B2 | 5/2009 | Fukuyama |
| 7,560,073 B1 | 7/2009 | Peters et al. |
| 7,625,712 B2 | 12/2009 | Paul et al. |
| 7,630,063 B2 | 12/2009 | Padmanabhan et al. |
| 7,674,598 B2 | 3/2010 | Paul et al. |
| 7,738,094 B2 | 6/2010 | Goldberg |
| 7,762,946 B2 | 7/2010 | Sugimoto |
| 7,781,226 B2 | 8/2010 | McDevitt et al. |
| 7,790,464 B2 | 9/2010 | Tarasev |
| 7,816,135 B2 | 10/2010 | Goldberg |
| 7,826,728 B2 | 11/2010 | Konno et al. |
| 7,854,891 B2 | 12/2010 | Yamamoto et al. |
| 7,892,551 B2 | 2/2011 | Glencross |
| 7,903,241 B2 | 3/2011 | Wardlaw et al. |
| 7,952,692 B2 | 5/2011 | Primack et al. |
| 8,009,894 B2 | 8/2011 | Lindberg et al. |
| 8,125,623 B2 | 2/2012 | Munger et al. |
| 8,224,058 B2 | 7/2012 | Lindberg et al. |
| 8,244,021 B2 | 8/2012 | Lett et al. |
| 8,306,594 B2 | 11/2012 | Paseman et al. |
| 8,353,848 B2 | 1/2013 | Long et al. |
| 8,358,405 B2 | 1/2013 | Kitamura et al. |
| 8,377,398 B2 | 2/2013 | McDevitt et al. |
| 8,406,859 B2 | 3/2013 | Zuzak et al. |
| 8,483,789 B2 | 7/2013 | Higgins |
| 8,488,903 B2 | 7/2013 | Higuchi |
| 8,541,227 B2 | 9/2013 | Christensen et al. |
| 8,630,016 B2 | 1/2014 | Swenson et al. |
| 8,753,890 B2 | 6/2014 | Lalpuria et al. |
| 9,693,723 B2 | 7/2017 | Ivosevic et al. |
| 2002/0143298 A1 | 10/2002 | Marsden |
| 2002/0164825 A1 | 11/2002 | Chen |
| 2003/0123047 A1 | 7/2003 | Pettersson et al. |
| 2003/0152927 A1 | 8/2003 | Jakobsen et al. |
| 2003/0170613 A1 | 9/2003 | Straus |
| 2003/0206828 A1 | 11/2003 | Bell |
| 2003/0230728 A1 | 12/2003 | Dai et al. |
| 2004/0048395 A1 | 3/2004 | Lee et al. |
| 2004/0224329 A1 | 11/2004 | Gjerde et al. |
| 2005/0054949 A1 | 3/2005 | McKinnon et al. |
| 2005/0139547 A1 | 6/2005 | Manoussakis et al. |
| 2005/0142565 A1 | 6/2005 | Samper et al. |
| 2005/0190058 A1 | 9/2005 | Call |
| 2005/0232813 A1 | 10/2005 | Karmali |
| 2006/0020531 A1 | 1/2006 | Veeneman et al. |
| 2006/0024756 A1 | 2/2006 | Tibbe et al. |
| 2006/0060531 A1 | 3/2006 | Coville et al. |
| 2006/0241495 A1 | 10/2006 | Kurtz |
| 2006/0252079 A1 | 11/2006 | Oldham et al. |
| 2007/0132994 A1 | 6/2007 | Kobayashi et al. |
| 2007/0178009 A1 | 8/2007 | Sakaino et al. |
| 2007/0196813 A1* | 8/2007 | Franzen ............ A61B 5/150786 435/4 |
| 2008/0047908 A1* | 2/2008 | Sekine ............. A61B 5/150213 210/787 |
| 2008/0190220 A1 | 8/2008 | Backes et al. |
| 2008/0203319 A1 | 8/2008 | Pentoney et al. |
| 2008/0268469 A1 | 10/2008 | Srienc et al. |
| 2009/0024060 A1 | 1/2009 | Darrigrand et al. |
| 2009/0075324 A1 | 3/2009 | Pettersson |
| 2009/0107903 A1 | 4/2009 | Dassa |
| 2009/0130646 A1 | 5/2009 | Fletcher et al. |
| 2009/0173685 A1 | 7/2009 | Imai et al. |
| 2009/0181411 A1 | 7/2009 | Battrell et al. |
| 2009/0259145 A1* | 10/2009 | Bartfeld ............. A61B 10/0096 600/576 |
| 2010/0285520 A1 | 11/2010 | Halverson et al. |
| 2010/0291599 A1 | 11/2010 | Tague, Jr. et al. |
| 2010/0294950 A1 | 11/2010 | Kitamura et al. |
| 2010/0314461 A1 | 12/2010 | Gruenbacher et al. |
| 2011/0106046 A1 | 5/2011 | Hiranuma et al. |
| 2011/0118139 A1 | 5/2011 | Mehta et al. |
| 2011/0159457 A1 | 6/2011 | Offermann |
| 2011/0159533 A1 | 6/2011 | Karkouche |
| 2011/0244581 A1 | 10/2011 | Nikonorov et al. |
| 2012/0016265 A1 | 1/2012 | Peterson et al. |
| 2012/0016307 A1 | 1/2012 | Burkholz et al. |
| 2012/0123297 A1 | 5/2012 | Brancazio |
| 2013/0045529 A1 | 2/2013 | Goldberg et al. |
| 2013/0076019 A1 | 3/2013 | Takemoto |
| 2013/0162990 A1 | 6/2013 | Kobayashi et al. |
| 2014/0073990 A1 | 3/2014 | Holmes et al. |
| 2014/0093896 A1 | 4/2014 | Mongale et al. |
| 2014/0200154 A1 | 7/2014 | Sugarman et al. |
| 2014/0269160 A1 | 9/2014 | Chee Mun |
| 2015/0112302 A1* | 4/2015 | Chattaraj ............... A61M 5/158 604/506 |
| 2015/0125882 A1 | 5/2015 | Bomheimer et al. |
| 2015/0125883 A1 | 5/2015 | Gordon et al. |
| 2015/0132789 A1 | 5/2015 | Bomheimer et al. |
| 2016/0100783 A1 | 4/2016 | Ivosevic et al. |

FOREIGN PATENT DOCUMENTS

| | | |
|---|---|---|
| CN | 102119017 A | 7/2011 |
| CN | 202141619 U | 2/2012 |
| CN | 103068307 A | 4/2013 |
| CN | 202928839 U | 5/2013 |
| CN | 203677610 U | 7/2014 |
| CN | 203785945 U | 8/2014 |
| CN | 205181357 U | 4/2016 |
| CN | 205317561 U | 6/2016 |
| EP | 0219053 A2 | 4/1987 |
| EP | 0545500 A1 | 6/1993 |
| EP | 0663070 B1 | 7/1995 |
| EP | 0681177 A1 | 11/1995 |
| EP | 0681177 B1 | 11/1995 |
| EP | 0737855 A1 | 10/1996 |
| EP | 0744600 A1 | 11/1996 |
| EP | 0788615 A1 | 8/1997 |
| EP | 0788615 B1 | 8/1997 |
| EP | 0800074 A1 | 10/1997 |
| EP | 0800074 B1 | 10/1997 |
| EP | 0818682 A2 | 1/1998 |
| EP | 0818682 B1 | 1/1998 |
| EP | 0821784 B1 | 11/1998 |
| EP | 0959346 A2 | 11/1999 |
| EP | 0969279 A2 | 1/2000 |
| EP | 0969279 B1 | 1/2000 |
| EP | 0809807 B1 | 7/2002 |
| EP | 1324021 A1 | 7/2003 |
| EP | 1324021 B1 | 7/2003 |
| EP | 1347702 A2 | 10/2003 |
| EP | 1456649 B1 | 6/2006 |
| EP | 1698883 A1 | 9/2006 |
| EP | 1698883 B1 | 9/2006 |
| EP | 1701150 A1 | 9/2006 |
| EP | 1767935 A1 | 3/2007 |
| EP | 1924195 A2 | 5/2008 |
| EP | 1990638 A1 | 11/2008 |
| EP | 2016390 A1 | 1/2009 |
| EP | 2041549 A1 | 4/2009 |
| EP | 2083687 A1 | 8/2009 |
| EP | 1405073 B1 | 3/2010 |
| EP | 2232442 A1 | 9/2010 |
| EP | 2298407 A1 | 3/2011 |
| EP | 2016390 B1 | 4/2013 |
| EP | 2586370 A2 | 5/2013 |
| EP | 2605020 A2 | 6/2013 |
| EP | 1558934 B1 | 7/2013 |
| EP | 2676606 A1 | 12/2013 |
| GB | 1595388 A | 8/1981 |
| JP | H10323341 A | 12/1998 |
| JP | 11318871 A | 11/1999 |
| JP | 200074906 A | 3/2000 |
| JP | 2000176006 A | 6/2000 |

(56) References Cited

FOREIGN PATENT DOCUMENTS

| | | | |
|---|---|---|---|
| JP | 200188098 A | 4/2001 |
| JP | 2001324500 A | 11/2001 |
| JP | 2002506208 A | 2/2002 |
| JP | 2002516982 A | 6/2002 |
| JP | 200319126 A | 1/2003 |
| JP | 200517280 A | 1/2005 |
| JP | 200517281 A | 1/2005 |
| JP | 2005006821 A | 1/2005 |
| JP | 2005524841 A | 8/2005 |
| JP | 2006208188 A | 8/2006 |
| JP | 2006317285 A | 11/2006 |
| JP | 2007-24522 * | 2/2007 |
| JP | 2007024522 A | 2/2007 |
| JP | 2007155441 A | 6/2007 |
| JP | 2007518978 A | 7/2007 |
| JP | 2008525768 A | 7/2008 |
| JP | 4255556 B2 | 2/2009 |
| JP | 2009525819 A | 7/2009 |
| JP | 2011133235 A | 7/2011 |
| JP | 2011529573 A | 12/2011 |
| JP | 2012132879 A | 7/2012 |
| JP | 2012137493 A | 7/2012 |
| JP | 2013096797 A | 5/2013 |
| JP | 2013524219 A | 6/2013 |
| JP | 2013545114 A | 12/2013 |
| NL | 6909366 A | 1/1970 |
| WO | 9920998 A1 | 4/1999 |
| WO | 9945384 A1 | 9/1999 |
| WO | 0028297 A2 | 5/2000 |
| WO | 0029847 A2 | 5/2000 |
| WO | 0244729 A1 | 6/2002 |
| WO | 0250518 A2 | 6/2002 |
| WO | 03036290 A1 | 5/2003 |
| WO | 2004100887 A2 | 11/2004 |
| WO | 2005100539 A2 | 10/2005 |
| WO | 2006047831 A1 | 5/2006 |
| WO | 2006096126 A1 | 9/2006 |
| WO | 2006119368 A2 | 11/2006 |
| WO | 2006124756 A2 | 11/2006 |
| WO | 2007012975 A1 | 2/2007 |
| WO | 2007033318 A2 | 3/2007 |
| WO | 2007051861 A1 | 5/2007 |
| WO | 2007111555 A1 | 10/2007 |
| WO | 2007129948 A1 | 11/2007 |
| WO | 2007145328 A1 | 12/2007 |
| WO | 2008002462 A2 | 1/2008 |
| WO | 2008010761 A1 | 1/2008 |
| WO | 2008037068 A2 | 4/2008 |
| WO | 2008103992 A2 | 8/2008 |
| WO | 2009091318 A1 | 7/2009 |
| WO | 2009093306 A1 | 7/2009 |
| WO | 2009155612 A3 | 12/2009 |
| WO | WO2009155612 A2 | 12/2009 |
| WO | 2010003518 A1 | 1/2010 |
| WO | 2010085658 A1 | 7/2010 |
| WO | 2011133540 A2 | 10/2011 |
| WO | 2012117648 A1 | 9/2012 |
| WO | 2013075031 A1 | 5/2013 |
| WO | 2013128177 A1 | 9/2013 |

* cited by examiner

BLOOD SAMPLE MANAGEMENT USING OPEN CELL FOAM

CROSS-REFERENCE TO RELATED APPLICATIONS

This application claims priority to U.S. Provisional Application Ser. No. 62/063,536, entitled "Blood Sample Management Using Open Cell Foam" filed Oct. 14, 2014, and U.S. Provisional Application Ser. No. 62/207,618, entitled "Blood Sample Management Using Open Cell Foam" filed Aug. 20, 2015, the entire disclosures of each of which are herein incorporated by reference.

BACKGROUND OF THE INVENTION

1. Field of the Disclosure

The present disclosure relates generally to a blood transfer device. More particularly, the present disclosure relates to a blood transfer device, a blood transfer and testing system, a lancet and blood transfer device, and a method of loading an anticoagulant.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Once collected, blood samples may be analyzed to obtain medically useful information including, for example, chemical composition, hematology, and coagulation.

Blood tests determine the physiological and biochemical states of the patient, such as disease, mineral content, drug effectiveness, and organ function. Blood tests may be performed in a clinical laboratory or at the point-of-care near the patient.

SUMMARY OF THE INVENTION

The present disclosure provides a specimen mixing and transfer device adapted to receive a sample. The specimen mixing and transfer device includes a housing, a material including pores that is disposed within the housing, and a dry anticoagulant powder within the pores of the material. In one embodiment, the material is a sponge material. In other embodiments, the material is an open cell foam. In one embodiment, the open cell foam is treated with an anticoagulant to form a dry anticoagulant powder finely distributed throughout the pores of the material. A blood sample may be received within the specimen mixing and transfer device. The blood sample is exposed to and mixes with the anticoagulant powder while passing through the material.

A specimen mixing and transfer device of the present disclosure offers uniform and passive blood mixing with an anticoagulant under flow-through conditions. A specimen mixing and transfer device of the present disclosure could catch blood clots or other contaminants within the microstructure of the material and prevent them from being dispensed into a diagnostic sample port. A specimen mixing and transfer device of the present disclosure enables a simple, low-cost design for passive flow-through blood stabilization. A specimen mixing and transfer device of the present disclosure enables precisely controlled loading of an anticoagulant into the material by soaking it with an anticoagulant and water solution and then drying the material to form a finely distributed dry anticoagulant powder throughout the pores of the material.

A specimen mixing and transfer device of the present disclosure may provide an effective passive blood mixing solution for applications wherein blood flows through a line. Such a specimen mixing and transfer device is useful for small blood volumes, e.g., less than 50 µL or less than 500 µL, and/or where inertial, e.g., gravity based, forces are ineffective for bulk manual mixing by flipping back and forth a blood collection container such as is required for vacuum tubes.

In accordance with an embodiment of the present invention, a specimen mixing and transfer device adapted to receive a sample includes a housing having a first end, a second end, and a sidewall extending therebetween; a material including pores and disposed within the housing; and a dry anticoagulant powder within the pores of the material.

In one configuration, the sample is a blood sample. In another configuration, the housing is adapted to receive the blood sample therein via the first end. In yet another configuration, with the blood sample received within the housing, the blood sample passes through the material thereby effectively mixing the blood sample with the dry anticoagulant powder. In one configuration, the blood sample dissolves and mixes with the dry anticoagulant powder while passing through the material. In another configuration, the material is an open cell foam. In yet another configuration, the material is a sponge. In one configuration, the first end includes an inlet. In another configuration, the second end includes an outlet. In yet another configuration, the housing defines a mixing chamber having a material including pores disposed within the mixing chamber. In one configuration, the housing includes an inlet channel in fluid communication with the inlet and the mixing chamber and an outlet channel in fluid communication with the mixing chamber and the outlet. In another configuration, the housing includes a dispensing chamber between the mixing chamber and the outlet.

In accordance with another embodiment of the present invention, a specimen mixing and transfer device adapted to receive a sample includes a housing having a first end, a second end, and a sidewall extending therebetween; a dry anticoagulant powder disposed within the housing; and a mixing element disposed within the housing.

In one configuration, the sample is a blood sample. In another configuration, the housing is adapted to receive the blood sample therein via the first end. In yet another configuration, with the blood sample received within the housing, the mixing element interferes with a flow of the blood sample to promote mixing of the blood sample with the dry anticoagulant powder. In one configuration, the dry anticoagulant powder is deposited on an interior surface of the housing. In another configuration, the mixing element comprises a plurality of posts. In one configuration, the first end includes an inlet. In another configuration, the second end includes an outlet. In yet another configuration, the housing defines a mixing chamber having a dry anticoagulant powder disposed within the mixing chamber. In one configuration, the housing includes an inlet channel in fluid communication with the inlet and the mixing chamber and an outlet channel in fluid communication with the mixing chamber and the outlet. In another configuration, the housing includes a dispensing chamber between the mixing chamber and the outlet. In yet another configuration, the housing includes two diverted flow channels between the inlet channel and the outlet channel.

In accordance with yet another embodiment of the present invention, a method of loading an anticoagulant to a material having pores includes soaking the material in a liquid solution of the anticoagulant and water; evaporating the water of the liquid solution; and forming a dry anticoagulant powder within the pores of the material.

In one configuration, the material is a sponge. In another configuration, the material is an open cell foam.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
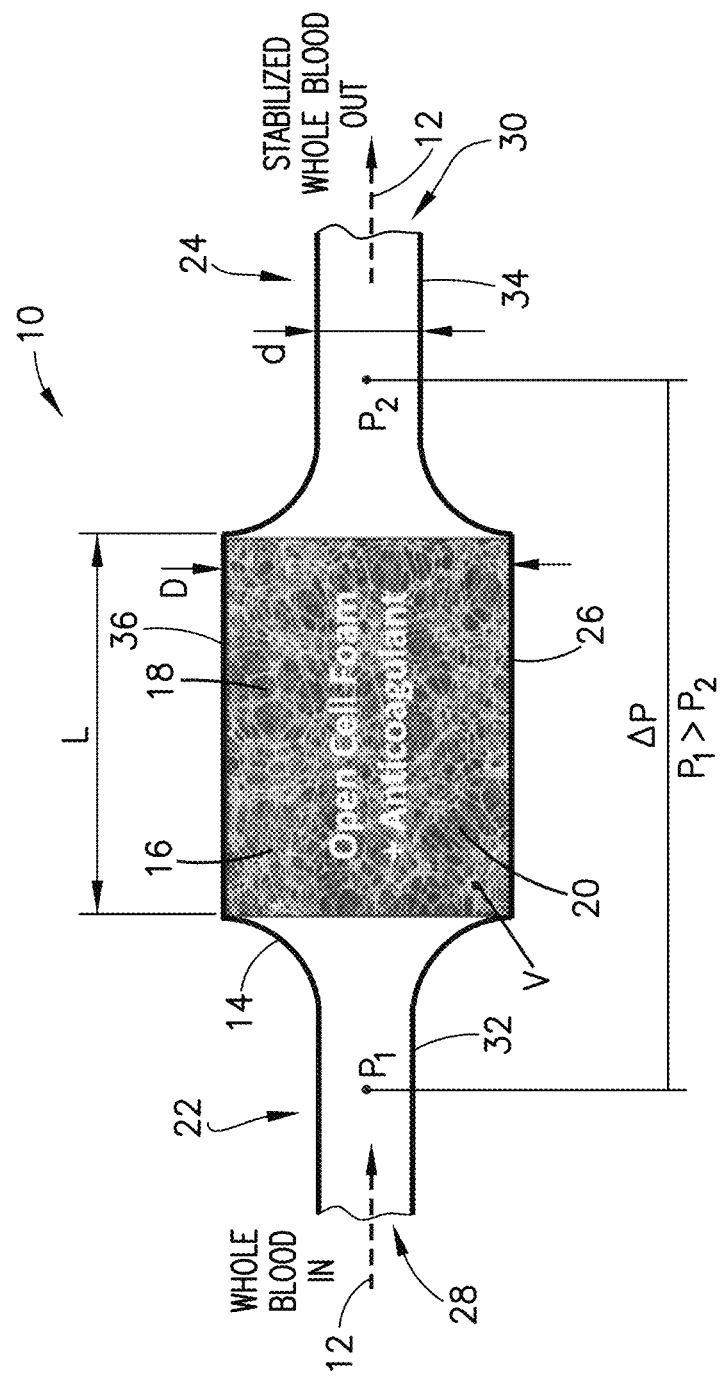
FIG. 1 is a partial cross-sectional view of a specimen mixing and transfer device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 2:
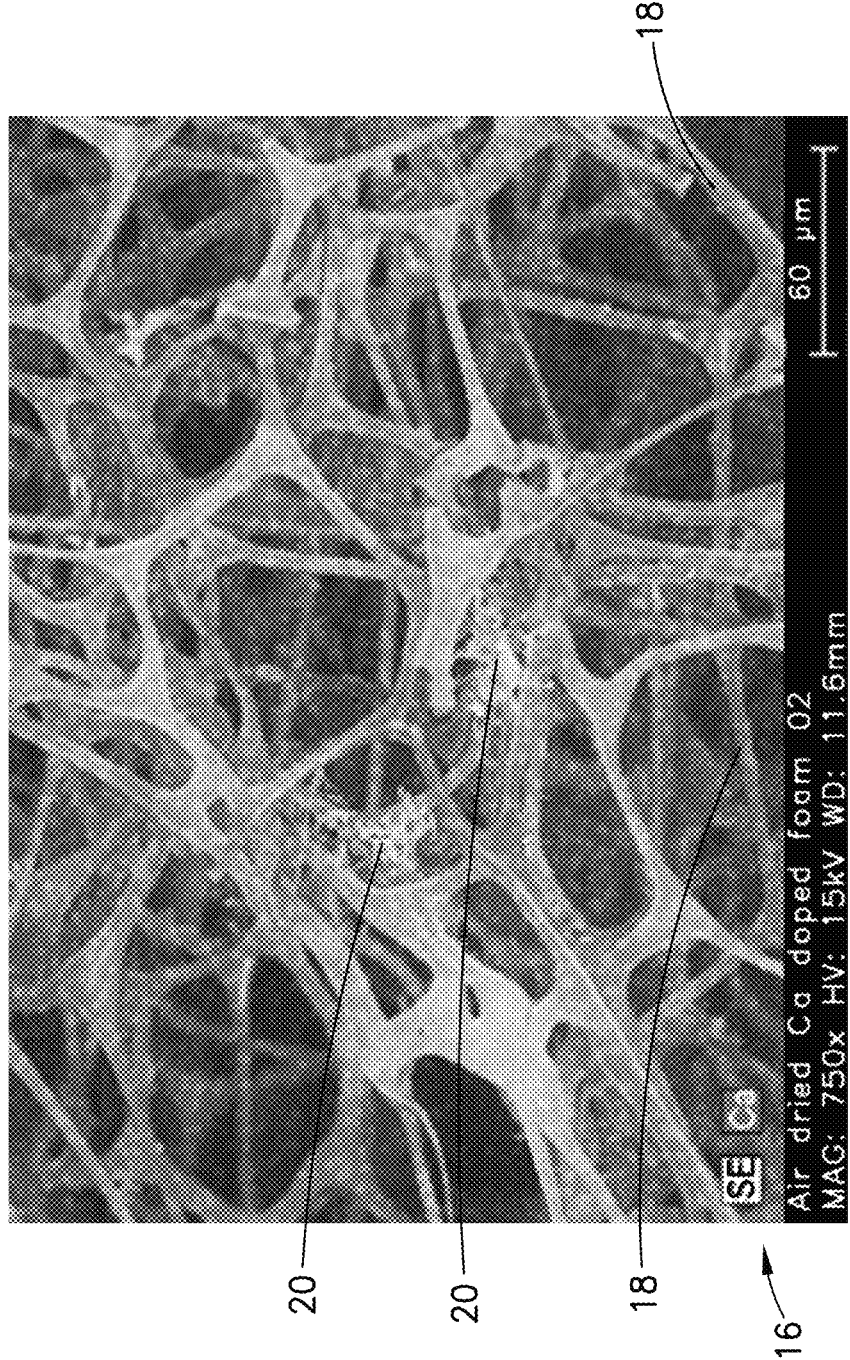
FIG. 2 is a microscopic view of the microstructure of an open cell foam material having a dry anticoagulant powder distributed throughout its microstructure in accordance with an embodiment of the present invention.
Figure 3:
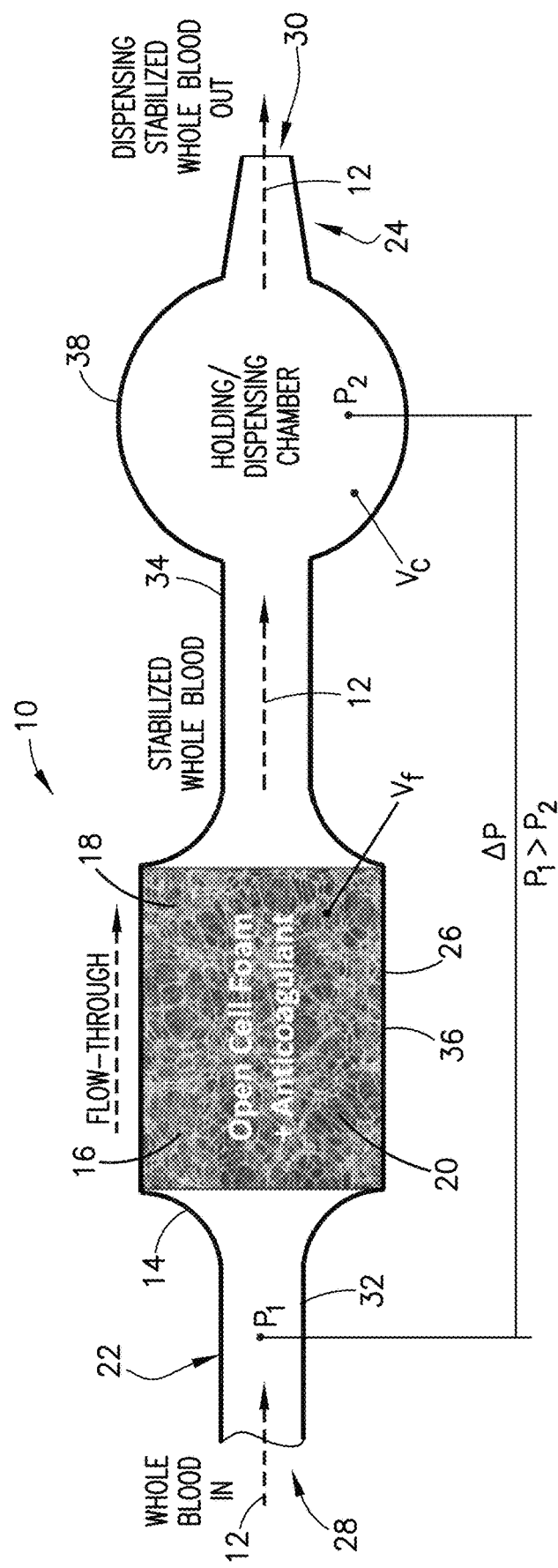
FIG. 3 is a partial cross-sectional view of a specimen mixing and transfer device in accordance with another embodiment of the present invention.

FIGS. 1-3 illustrate exemplary embodiments of a specimen mixing and transfer device of the present disclosure. The specimen mixing and transfer device 10 is adapted to receive a sample 12. In one embodiment, the specimen mixing and transfer device 10 includes a housing 14, a material 16 including pores 18 that is disposed within the housing 14, and a dry anticoagulant powder 20 within the pores 18 of the material 16.

With a sample 12 received within the specimen mixing and transfer device 10, a portion of the specimen mixing and transfer device 10 acts as a flow-through chamber for the effective mixing of a sample 12 with the dry anticoagulant powder 20 within the material 16. In other embodiments, the material 16 may contain other dry substances. The effective mixing is achieved by passing the sample 12 through the material 16 having the dry anticoagulant powder 20 distributed throughout its microstructure.

A specimen mixing and transfer device 10 of the present disclosure offers uniform and passive blood mixing with an anticoagulant under flow-through conditions. A specimen mixing and transfer device 10 of the present disclosure may catch blood clots or other contaminants within the microstructure of the material 16 and prevent them from being dispensed into a diagnostic sample port. A specimen mixing and transfer device 10 of the present disclosure enables a simple, low cost design for passive flow-through blood stabilization. A specimen mixing and transfer device 10 of the present disclosure enables precisely controlled loading of an anticoagulant into the material 16 by soaking it with an anticoagulant and water solution and then drying the material 16 to form a finely distributed dry anticoagulant powder 20 throughout the pores 18 of the material 16.

A specimen mixing and transfer device 10 of the present disclosure may provide an effective passive blood mixing solution for applications wherein blood flows through a line. Such a specimen mixing and transfer device 10 is useful for small blood volumes, e.g., less than 50 μL, or less than 500 μL, and/or where inertial, e.g., gravity based, forces are ineffective for bulk manual mixing by flipping back and forth a blood collection container such as is required for vacuum tubes.

FIG. 1 illustrates an exemplary embodiment of a specimen mixing and transfer device 10 of the present disclosure. Referring to FIG. 1, in one embodiment, a specimen mixing and transfer device 10 includes a housing 14, a material 16 including pores 18 that are disposed within the housing 14, and a dry anticoagulant powder 20 within the pores 18 of the material 16. The housing 14 includes a first end 22, a second end 24, and a sidewall 26 extending between the first end 22 and the second end 24. In one embodiment, the first end 22 includes an inlet 28 and the second end 24 includes an outlet 30.

Referring to FIG. 1, in one embodiment, the housing 14 of the specimen mixing and transfer device 10 includes an inlet channel 32 and an outlet channel 34. The inlet channel 32 and the outlet channel 34 are in fluid communication via a flow channel or mixing chamber 36. For example, the inlet channel 32 is in fluid communication with the inlet 28 and the mixing chamber 36; and the outlet channel 34 is in fluid communication with the mixing chamber 36 and the outlet 30. In one embodiment, the material 16 is disposed within the mixing chamber 36 of the housing 14.

In one embodiment, the material 16 is a sponge material. In other embodiments, the material 16 is an open cell foam. In one embodiment, the open cell foam is treated with an anticoagulant, as described in detail below, to form a dry anticoagulant powder 20 finely distributed throughout the pores 18 of the material 16. A sample 12 may be received within the specimen mixing and transfer device 10. In some embodiments, the sample 12 gets soaked into the material 16 based on capillary principles. In some embodiments, the sample 12 may be a blood sample. The blood sample is exposed to and mixes with the anticoagulant powder 20 while passing through the intricate microstructure of the material 16. In this manner, the specimen mixing and transfer device 10 produces a stabilized sample. In some embodiments, the stabilized sample may be transferred to a diagnostic instrument such as a blood testing device, a point-of-care testing device, or similar analytical device.

In one embodiment, the material 16 is an open cell foam. For example, the material 16 is a soft deformable open cell foam that is inert to blood. In one embodiment, the open cell foam may be a melamine foam, such as Basotect® foam commercially available from BASF. In another embodiment, the open cell foam may consist of a formaldehyde-melamine-sodium bisulfite copolymer. The open cell foam may be a flexible, hydrophilic open cell foam that is resistant to heat and many organic solvents. In one embodiment, the open cell foam may be a sponge material.

A method of loading an anticoagulant to a material 16 having pores 18 will now be discussed. In one embodiment, the method includes soaking the material 16 in a liquid solution of the anticoagulant and water; evaporating the water of the liquid solution; and forming a dry anticoagulant powder 20 within the pores 18 of the material 16.

The method of the present disclosure enables precisely controlled loading of an anticoagulant into the material 16 by soaking it with an anticoagulant and water solution and then drying the material 16 to form a finely distributed dry anticoagulant powder 20 throughout the pores 18 of the material 16, as shown in FIG. 2.

Anticoagulants such as Heparin or EDTA (Ethylene Diamine Tetra Acetic Acid), as well as other blood stabilization agents, could be introduced into the material 16 as a liquid solution by soaking the material 16 in the liquid solution of a desired concentration. After evaporating the liquid phase, e.g., evaporating the water from a water and Heparin solution, a dry anticoagulant powder 20 is formed and finely distributed throughout the internal structure of the material 16, as shown in FIG. 2. For example, the dry anticoagulant powder 20 is formed and finely distributed throughout the pores 18 of the material 16. In a similar manner, the material 16 could be treated to provide a hydrophobic, hydrophilic, or reactive internal pore surface.

In one configuration, a key advantage of providing an open cell foam as the material 16 is that a known amount of anticoagulant may be loaded into the pores 18 of the foam material. A desired concentration of an anticoagulant may be dissolved in water or other suitable solvent and then introduced into the pores 18 of the open cell foam material 16 in liquid form. In one embodiment, the anticoagulant may be loaded into the pores 18 by dipping the open cell foam material 16 into a solution of anticoagulant and water or solvent and subsequently allowing the open cell foam material 16 to dry. The open cell foam material 16 may be allowed to dry in ambient air or in a heated oven. After drying, the anticoagulant may be distributed throughout the internal microstructure of the open cell foam material 16 in the form of a dry powder.

It is noted that suitable hydrophilic foam material having interconnected cell pores may be loaded with anticoagulant, as described above, and used as described herein for flow-through blood stabilization.

One key advantage of using a melamine-based open cell foam material is that melamine foams have a generally low analyte bias. As discussed herein, analyte bias is the difference in a measured value of an analyte as compared to a blood control value. Generally, analyte bias occurs when analytes adhere to a surface of a material, when analytes are leached from a material, via introduction of other components which may interfere with a measurement, or upon activation of a biological process. Additional open cell foam materials which are suitable for use as described herein include organic thermoplastic and thermosetting polymers and co-polymers, including but not limited to polyolefins, polyimides, polyamides, such as polyethylene terephthalate (PET), polypropylene (PP), polyethylene (PE), and the like. The material may be in fibrous structure, such as woven or random fiber form, or irregular 3D structure.

In order to avoid or minimize potential analyte bias associated with the housing 14 of the transfer device 10, the material of the housing 14 may be treated. In one embodiment, the housing 14 may be treated with an additive coating which acts to block analytes from sticking to a surface. Additive coatings may include, but are not limited to, 1.) proteins, such as bovine serum albumin (BSA), casein, or non-fat milk, 2.) surfactants such as polysorbate 20 (Tween 20) and organosilicone (L-720), 3.) polymers and copolymers such as polyethylene glycol (PEG), polyvinyl alcohol (PVA), and polyvinylpyrrolidone (PVP), 4.) carbohydrates such as destran and glycosamino glycans, such as heparin, and 5.) cell membrane mimicking polymers such as Lipidure.

Alternatively, the housing 14 may be treated with a chemical surface modification. Chemical surface modifications can include, but are not limited to, 1.) gas plasma treatment, 2.) chemical bonding or polyethylene glycol (PEG) or other polymers to achieve a desired hydrophobicity or hydrophilicity, 3.) chemical modification of the surface to include hydrophilic compositions such as ethylene glycol, or hydrophobic groups, such as long carbon chains, and 4.) vapor deposition of a substance, such as parylene. It is appreciated herein that combinations of any of the above materials may be used to achieve the desired properties to minimize analyte bias for a specific analyte or group of analytes.

In one embodiment, the mixing chamber 36 includes the material 16 having a dry anticoagulant powder 20 therein. For example, referring to FIGS. 1 and 3, the material 16 is disposed within the mixing chamber 36 of the specimen mixing and transfer device 10. The anticoagulant can be loaded into the material 16 having pores 18 as described above.

Referring to FIG. 1, the housing 14 of the specimen mixing and transfer device 10 is adapted to receive a sample 12 therein via the first end 22. For example, the housing 14 of the specimen mixing and transfer device 10 is adapted to receive a sample 12 therein via the inlet 28. After the sample 12 enters the specimen mixing and transfer device 10 via the inlet 28, the sample 12 flows through the inlet channel 32 to the mixing chamber 36.

With the sample 12 received within the mixing chamber 36, the mixing chamber 36 acts as a flow-through chamber for the effective mixing of a sample 12 with the dry anticoagulant powder 20 within the material 16. In other embodiments, the material 16 may contain other dry substances. The effective mixing is achieved by passing the sample 12 through the material 16 having the dry anticoagulant powder 20 distributed throughout its microstructure. The sample 12 dissolves and mixes with the dry anticoagulant powder 20 while passing through the material 16.

Referring to FIG. 2, a view of the microstructure of the material 16 having a dry anticoagulant powder 20 distributed throughout its microstructure, e.g., its pores 18, is illustrated.

Referring to FIG. 3, in one embodiment, the housing 14 of the specimen mixing and transfer device 10 includes a dispensing chamber or holding chamber 38. The dispensing chamber 38 may be adjacent the outlet 30 of the specimen mixing and transfer device 10. For example, the dispensing chamber 38 may be disposed between the mixing chamber 36 and the outlet 30.

After the blood sample is exposed to and mixes with the anticoagulant powder 20 while passing through the intricate microstructure of the material 16, a stabilized sample flows from the material 16 to the dispensing chamber 38 via the outlet channel 34. The stabilized sample can remain within the dispensing chamber 38 until it is desired to transfer the stabilized sample from the specimen mixing and transfer device 10. For example, the stabilized sample may be transferred to a diagnostic instrument such as a blood testing device, a point-of-care testing device, or similar analytical device.

FIGS. 4-10 illustrate other exemplary embodiments of a specimen mixing and transfer device of the present disclosure. Referring to FIGS. 4-10, a specimen mixing and transfer device of the present disclosure may also be effective with small blood volumes that are typically associated with laminar flow conditions that require flow obstacles to promote mixing with a dry anticoagulant deposited on the walls of the flow-through structure.

Figure 4:
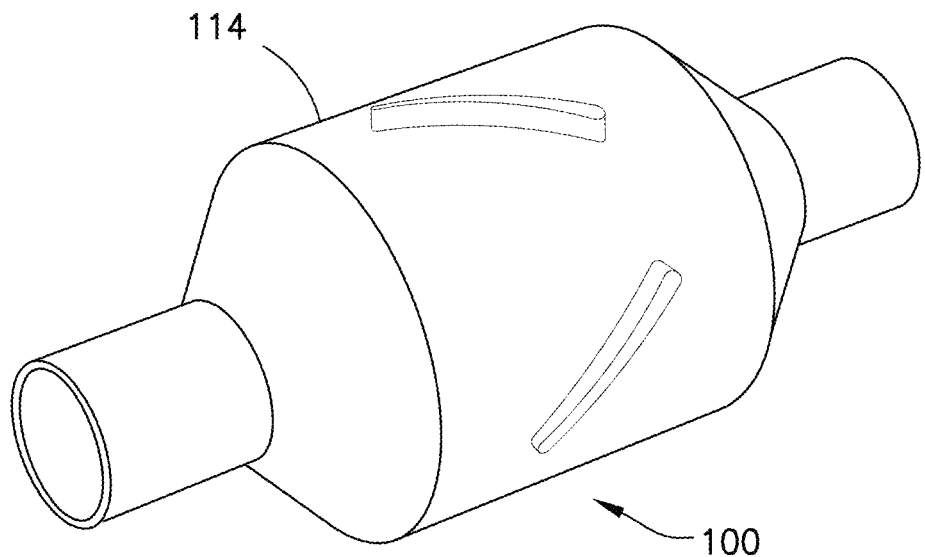
FIG. 4 is a perspective view of a specimen mixing and transfer device in accordance with an embodiment of the present invention.
Figure 6:
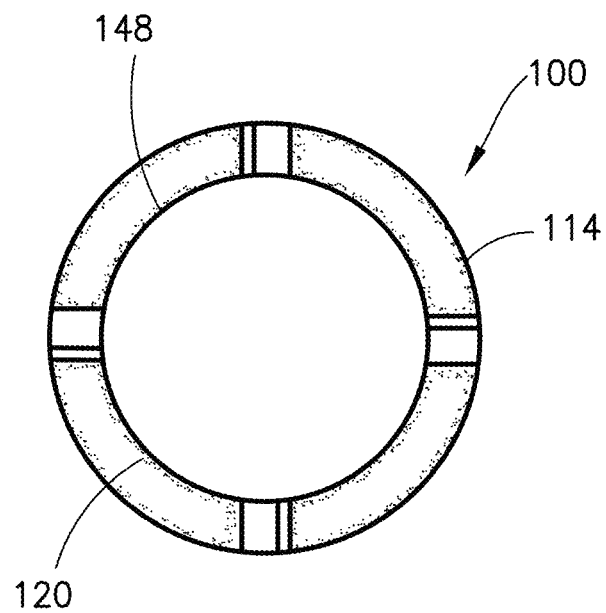
FIG. 6 is a partial cross-sectional view taken along line 6-6 of FIG. 5 in accordance with an embodiment of the present invention.
Figure 5:
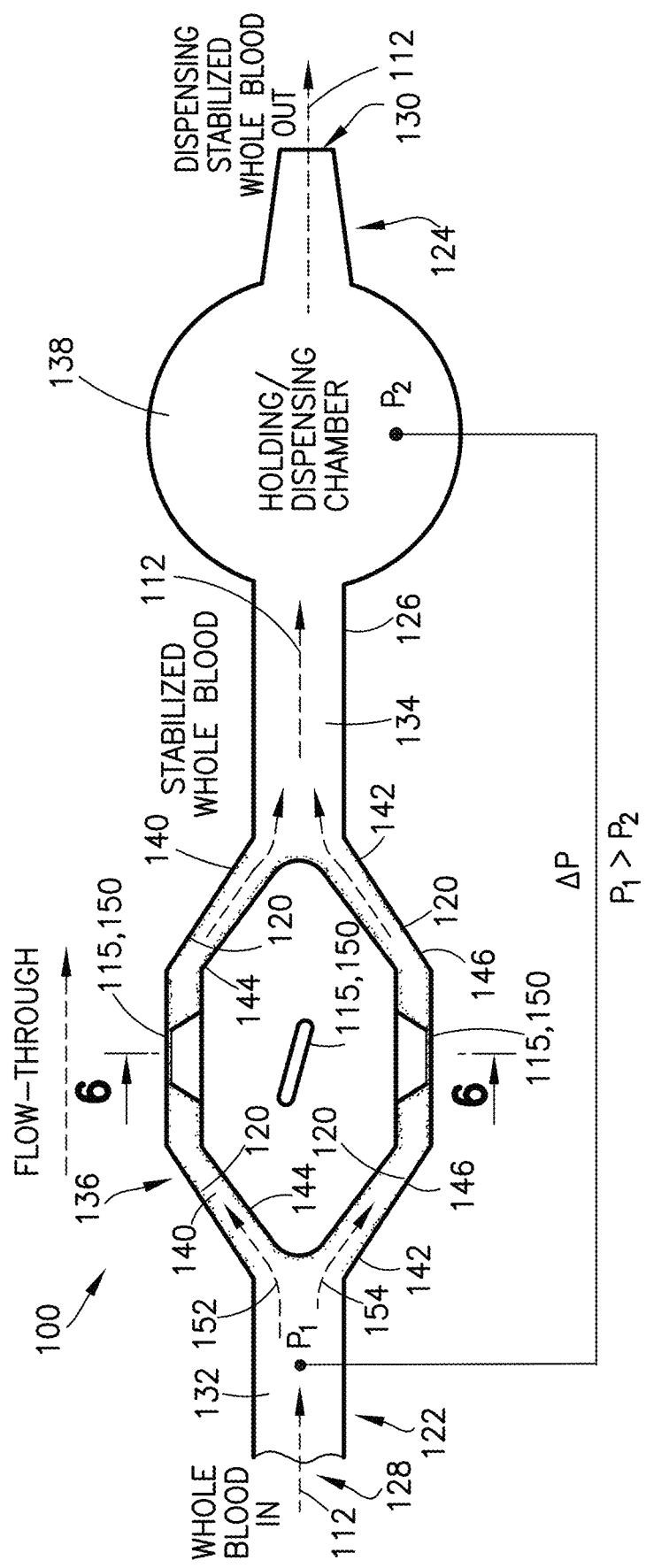
FIG. 5 is a partial cross-sectional view of a specimen mixing and transfer device in accordance with an embodiment of the present invention.
Figure 9:
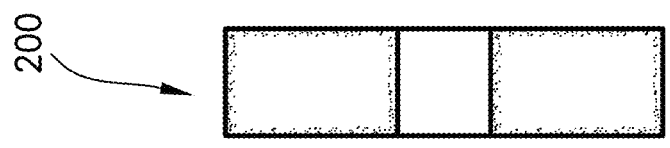
FIG. 9 is a partial cross-sectional view taken along line 9-9 of FIG. 8 in accordance with an embodiment of the present invention.

FIGS. 4-6 illustrate another exemplary embodiment of a specimen mixing and transfer device of the present disclosure. The specimen mixing and transfer device 100 is adapted to receive a sample 112. In some embodiments, the sample 112 may be a blood sample. In one embodiment, the specimen mixing and transfer device 100 includes a housing 114, a dry anticoagulant powder 120 disposed within the housing 114, and a mixing element 115 disposed within the housing 114.

The housing 114 includes a first end 122, a second end 124, and a sidewall 126 extending between the first end 122 and the second end 124. In one embodiment, the first end 122 includes an inlet 128 and the second end 124 includes an outlet 130.

Referring to FIG. 5, in one embodiment, the housing 114 of the specimen mixing and transfer device 100 includes an inlet channel 132 and an outlet channel 134. The inlet channel 132 and the outlet channel 134 are in fluid communication via a flow channel or mixing chamber 136. For example, the inlet channel 132 is in fluid communication with the inlet 128 and the mixing chamber 136; and the outlet channel 134 is in fluid communication with the mixing chamber 136 and the outlet 130. In one embodiment, the dry anticoagulant powder 120 is disposed within the mixing chamber 136 of the housing 114.

In one embodiment, the inlet channel 132 and the outlet channel 134 are in fluid communication via a first flow channel 140 and a second flow channel 142. For example, the inlet channel 132 may branch off into two separate flow channels, e.g., the first flow channel 140 and the second flow channel 142. The two separate flow channels, e.g., the first flow channel 140 and the second flow channel 142, may both flow into the outlet channel 134 as shown in FIG. 5.

The first flow channel 140 includes walls 144 and the second flow channel 142 includes walls 146. In one embodiment, a first portion of the dry anticoagulant powder 120 is deposited on walls 144 and a second portion of the dry anticoagulant powder 120 is deposited on walls 146. For example, in one embodiment, a first portion of the dry anticoagulant powder 120 is deposited on an interior surface 148 of the housing 114, e.g., an interior surface of wall 144, and a second portion of the dry anticoagulant powder 120 is deposited on an interior surface 148 of the housing 114, e.g., an interior surface of wall 146.

Referring to FIG. 5, in one embodiment, the housing 114 of the specimen mixing and transfer device 100 includes a dispensing chamber or holding chamber 138. The dispensing chamber 138 may be adjacent to the outlet 130 of the specimen mixing and transfer device 100. For example, the dispensing chamber 138 may be disposed between the mixing chamber 136 and the outlet 130. In one embodiment, the dispensing chamber 138 may be positioned between the flow channels 140, 142 and the outlet 130.

In one embodiment, the specimen mixing and transfer device 100 includes a mixing element 115 disposed within the housing 114. For example, a portion of the mixing chamber 136 may also include obstacles or mixing promoters 150 that interfere with the flow path of the blood sample thereby promoting mixing between the blood sample and the dry anticoagulant powder 120. In some embodiments, a portion of the first flow channel 140 and a portion of the second flow channel 142 may include obstacles or mixing promoters 150 that interfere with the flow path of the blood sample thereby promoting mixing between the blood sample and the dry anticoagulant powder 120.

Referring to FIGS. 4-6, the specimen mixing and transfer device 100 is adapted to receive a sample 112 therein via the first end 122. For example, the housing 114 of the specimen mixing and transfer device 100 is adapted to receive a sample 112 therein via the inlet 128. The sample 112 flows into the inlet 128 and to the inlet channel 132. In some embodiments, the sample 112 may be a blood sample.

With the blood sample received within the inlet channel 132, a first portion 152 of the blood sample flows to the first flow channel 140 and a second portion 154 of the blood sample flows to the second flow channel 142. The first flow channel 140 provides a first flow path for the first portion 152 of the blood sample and the second flow channel 142 provides a second flow path for the second portion 154 of the blood sample.

With the first portion 152 of the blood sample received within the first flow channel 140, the first portion 152 of the blood sample mixes with a first portion of the dry anticoagulant powder 120 deposited on the walls 144 of the first flow channel 140. The first flow channel 140 may also include obstacles or mixing promoters 150 that interfere with the flow path of the blood sample thereby promoting mixing between the blood sample and the first portion of the dry anticoagulant powder 120. After mixing, the first portion 152 of the blood sample and the first portion of the dry anticoagulant powder 120, i.e., a stabilized blood sample, travel to the outlet channel 134.

With the second portion 154 of the blood sample received within the second flow channel 142, the second portion 154 of the blood sample mixes with a second portion of the dry anticoagulant powder 120 deposited on the walls 146 of the second flow channel 142. The second flow channel 142 may also include obstacles or mixing promoters 150 that interfere with the flow path of the blood sample thereby promoting mixing between the blood sample and the second portion of the dry anticoagulant powder 120. After mixing, the second portion 154 of the blood sample and the second portion of the dry anticoagulant powder 120, i.e., a stabilized blood sample, travel to the outlet channel 134.

In other embodiments, other portions of the specimen mixing and transfer device 100 may also include obstacles or mixing promoters 150 that interfere with the flow path of the blood sample thereby promoting mixing between the blood sample and the dry anticoagulant powder 120.

Figure 7:
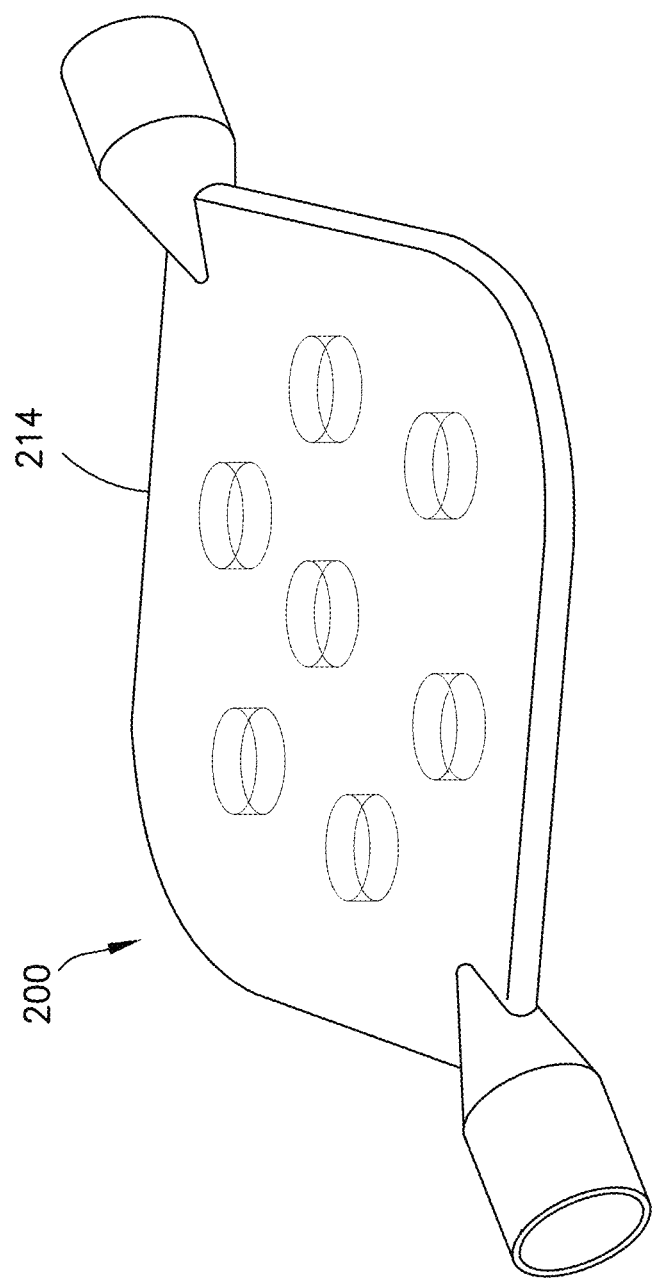
FIG. 7 is a perspective view of a specimen mixing and transfer device in accordance with another embodiment of the present invention.
Figure 8:
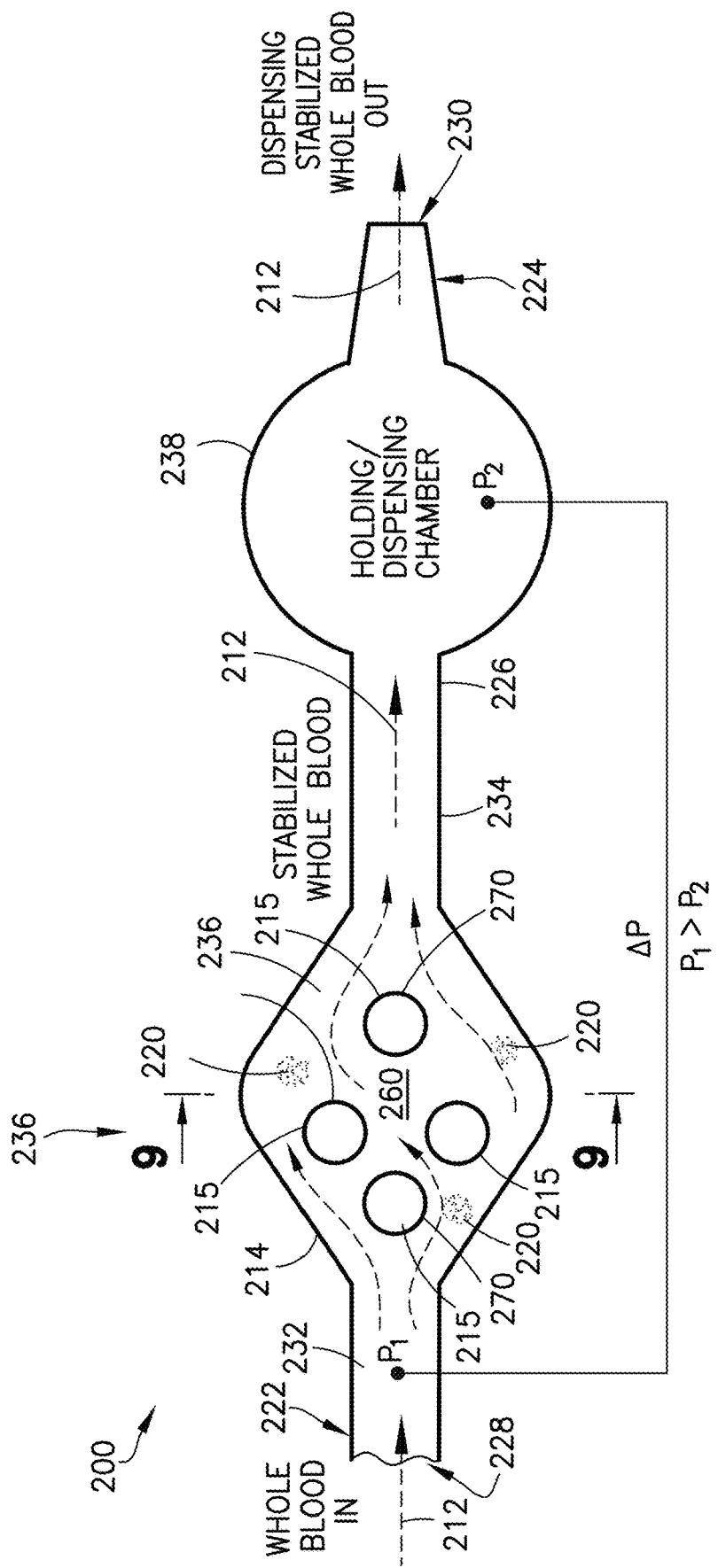
FIG. 8 is a partial cross-sectional view of a specimen mixing and transfer device in accordance with another embodiment of the present invention.

FIGS. 7-10 illustrate other exemplary embodiments of a specimen mixing and transfer device of the present disclosure. Referring to FIGS. 7 and 8, the specimen mixing and transfer device 200 is adapted to receive a sample 212. In some embodiments, the sample 212 may be a blood sample. In one embodiment, the specimen mixing and transfer device 200 includes a housing 214, a dry anticoagulant powder 220 disposed within the housing 214, and a mixing element 215 disposed within the housing 214.

The housing 214 includes a first end 222, a second end 224, and a sidewall 226 extending between the first end 222 and the second end 224. In one embodiment, the first end 222 includes an inlet 228 and the second end 224 includes an outlet 230.

Referring to FIG. 8, in one embodiment, the housing 214 of the specimen mixing and transfer device 200 includes an inlet channel 232 and an outlet channel 234. The inlet channel 232 and the outlet channel 234 are in fluid communication via a flow channel or mixing chamber 236. For example, the inlet channel 232 is in fluid communication with the inlet 228 and the mixing chamber 236; and the outlet channel 234 is in fluid communication with the mixing chamber 236 and the outlet 230. In one embodiment, the dry anticoagulant powder 220 is disposed within the mixing chamber 236 of the housing 214. In one embodiment, the dry anticoagulant powder 220 is deposited on an interior surface 260 of the housing 214.

Referring to FIG. 8, in one embodiment, the housing 214 of the specimen mixing and transfer device 200 includes a dispensing chamber or holding chamber 238. The dispensing chamber 238 may be adjacent to the outlet 230 of the specimen mixing and transfer device 200. For example, the dispensing chamber 238 may be disposed between the mixing chamber 236 and the outlet 230.

In one embodiment, the specimen mixing and transfer device 200 includes a mixing element 215 disposed within the housing 214. In one embodiment, the mixing element 215 includes a plurality of posts 270. For example, the mixing chamber 236 may include a plurality of posts 270 that interfere with the flow path of the blood sample thereby promoting mixing between the blood sample and the dry anticoagulant powder 220.

Referring to FIGS. 7 and 8, the specimen mixing and transfer device 200 is adapted to receive a sample 212 therein via the first end 222. For example, the housing 214 of the specimen mixing and transfer device 200 is adapted to receive a sample 212 therein via the inlet 228. The sample 212 flows into the inlet 228 and to the inlet channel 232. In some embodiments, the sample 212 may be a blood sample.

With the blood sample received within the inlet channel 232, the blood sample flows into the mixing chamber 236. As the blood sample flows into the mixing chamber 236, the blood sample mixes with the dry anticoagulant powder 220 deposited on an interior surface 260 of the housing 214. The mixing chamber 236 may include the plurality of posts 270 that interfere with the flow path of the blood sample thereby promoting mixing between the blood sample and the dry anticoagulant powder 220. After mixing, the blood sample and the dry anticoagulant powder 220, i.e., a stabilized blood sample, travel to the outlet channel 234.

In other embodiments, other portions of the specimen mixing and transfer device 200 may also include mixing elements 215 that interfere with the flow path of the blood sample thereby promoting mixing between the blood sample and the dry anticoagulant powder 220.

Figure 10:
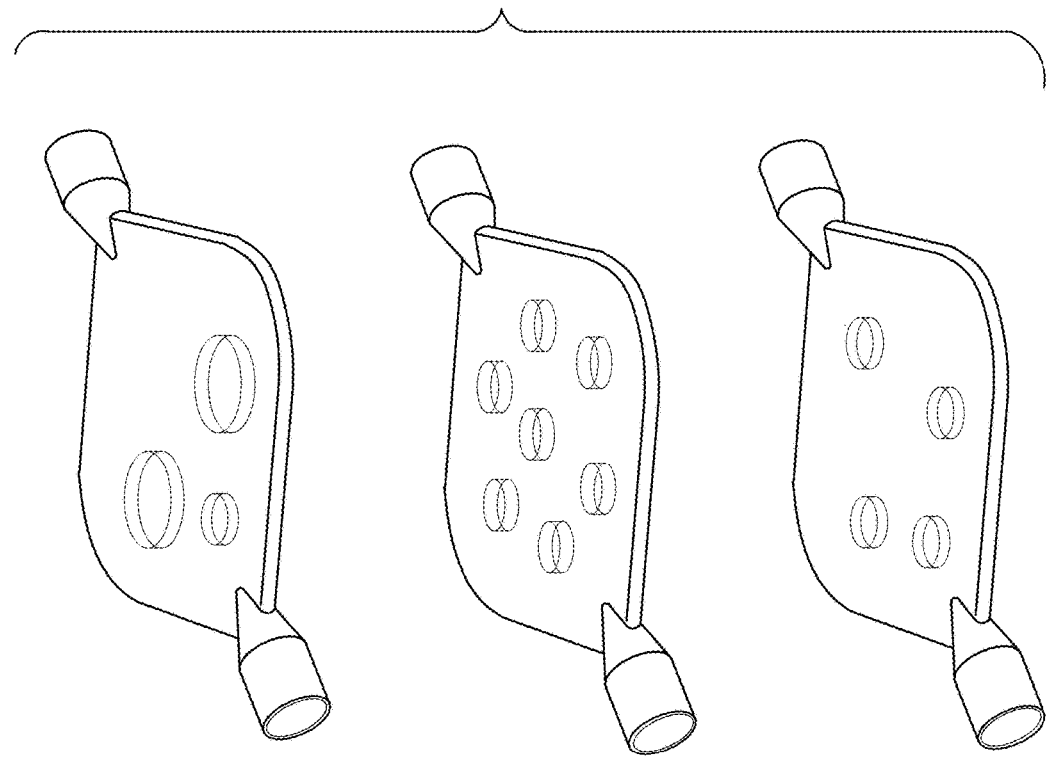
FIG. 10 is a perspective view of alternate embodiments of a specimen mixing and transfer device in accordance with another embodiment of the present invention.
Figure 10:
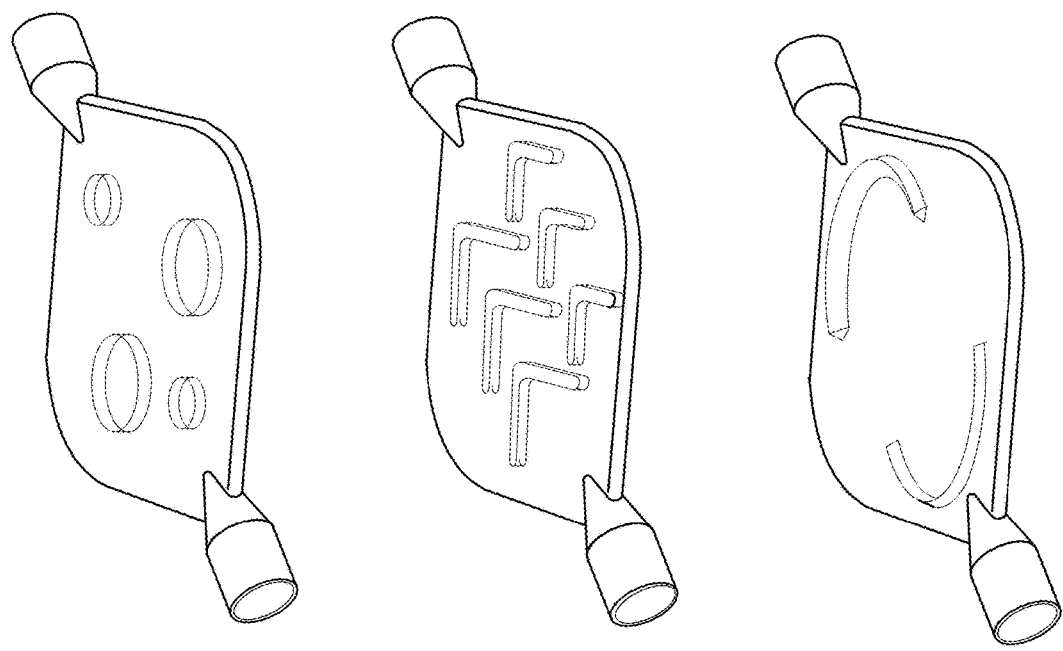
Figure 11A:
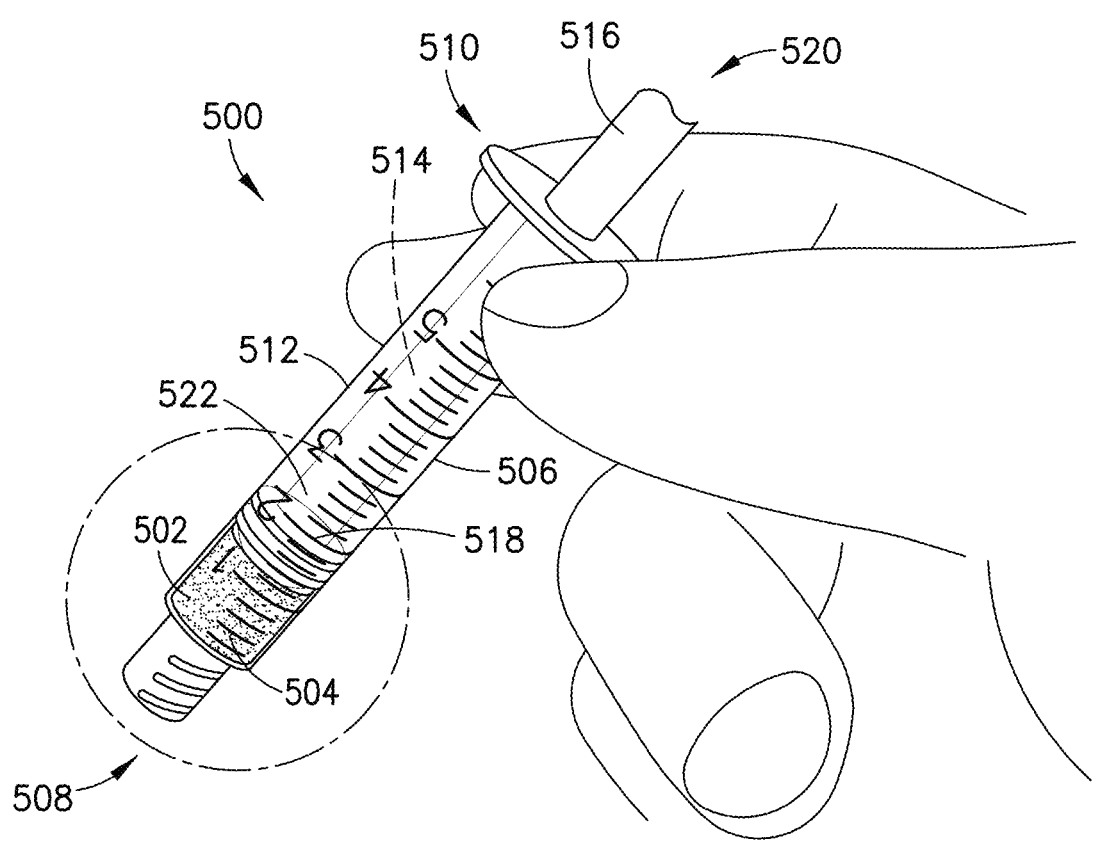
FIG. 11A is a perspective view of a syringe assembly in accordance with an embodiment of the present invention.
Figure 11B:
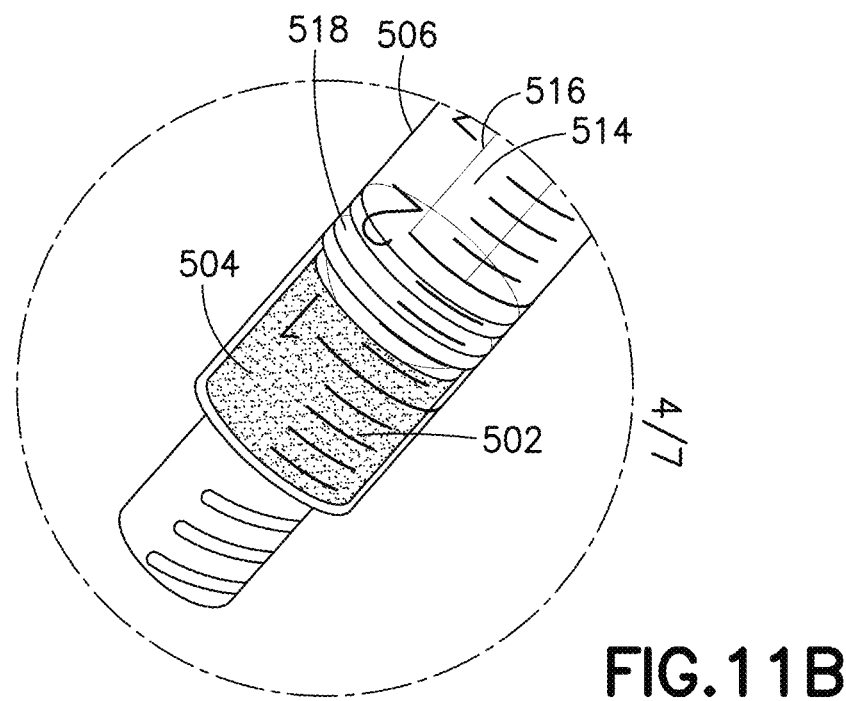
FIG. 11B is a close-up partial perspective view of the syringe assembly of FIG. 11A in accordance with an embodiment of the present invention.
Figure 11C:
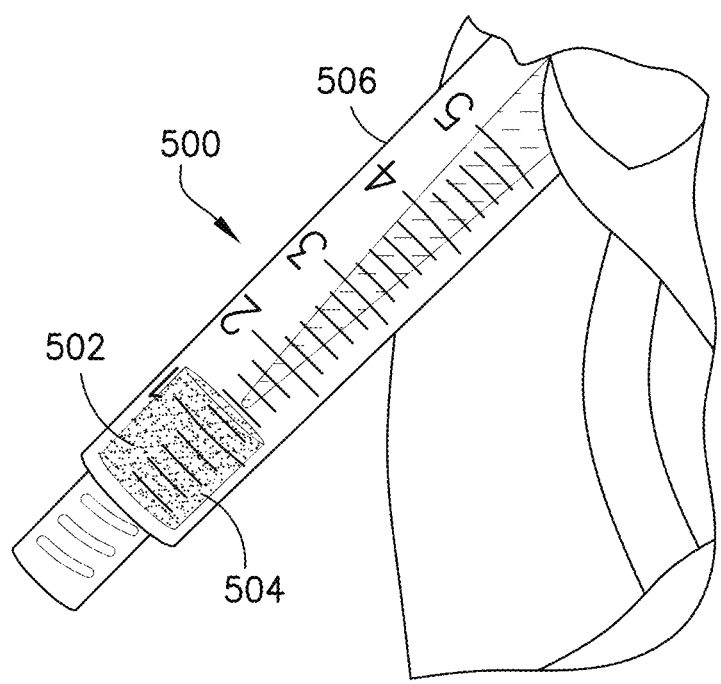
FIG. 11C is a perspective view of a syringe assembly in accordance with an embodiment of the present invention.
Figure 12:
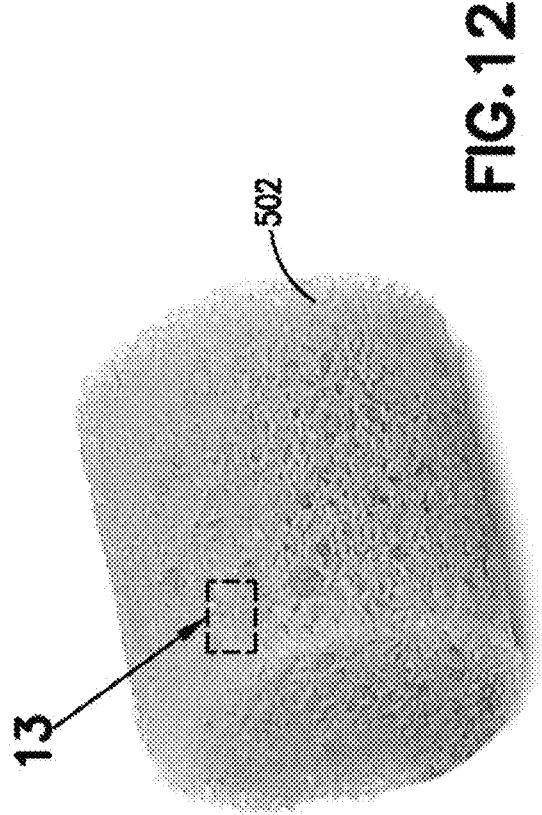
FIG. 12 is a perspective view of an open cell foam material in accordance with an embodiment of the present invention.

Referring to FIG. 10, alternate embodiments of a specimen mixing and transfer device of the present disclosure are illustrated.

FIGS. 11A-16 illustrate another exemplary embodiment of a material of the present disclosure. The material 502 includes pores 505 and has a dry anticoagulant powder 504 within the pores 505 of the material 502, as described above. In one embodiment, the material 502 is a sponge material. In other embodiments, the material 502 is an open cell foam. In one embodiment, the open cell foam is treated with an anticoagulant, as described in detail above, to form a dry anticoagulant powder 504 finely distributed throughout the pores 505 of the material 502.

In one embodiment, the material 502 is an open cell foam. For example, the material 502 is a soft deformable open cell foam that is inert to blood. In one embodiment, the open cell foam may be a melamine foam, such as Basotect® foam commercially available from BASF. In another embodiment, the open cell foam may consist of a formaldehyde-melamine-sodium bisulfite copolymer. The open cell foam may be a flexible, hydrophilic open cell foam that is resistant to heat and many organic solvents. In one embodiment, the open cell foam may be a sponge material.

Referring to FIGS. 11A-16, the material 502 can be utilized with a syringe assembly 500. The syringe assembly 500 may include an open cell foam material 502 having a dry anticoagulant powder 504 therein. The open cell foam material 502 is disposed within the syringe assembly 500. The anticoagulant can be loaded into the open cell foam material 502 having pores 505, as described above.

In one embodiment, the syringe assembly 500 includes a syringe barrel 506 having a first end 508, a second end 510, and a sidewall 512 extending therebetween and defining an interior 514. Referring to FIGS. 11A-11C and 15, the open cell foam material 502 is disposed within the interior 514 of the syringe barrel 506.

In one embodiment, the syringe assembly 500 includes a plunger rod 516 and a stopper 518. The plunger rod 516 includes a first end 520 and a second end 522. The stopper 518 is engaged with the second end 522 of the plunger rod 516 and is slidably disposed within the interior 514 of the syringe barrel 506. The stopper 518 is sized relative to the interior 514 of the syringe barrel 506 to provide sealing engagement with the sidewall 512 of the syringe barrel 506.

The open cell foam material 502 is placed in the syringe barrel 506 for mixing and stabilizing blood. The blood gets collected in the syringe barrel 506 with the open cell foam material 502 embedded inside the syringe barrel 506. The stabilized blood can then be dispensed for analysis. In one embodiment, the syringe assembly 500 is an arterial blood gas syringe and the stabilized blood can be dispensed for blood gas analysis.

In one embodiment, the syringe assembly 500 acts as a flow-through chamber for the effective mixing of a blood sample with the dry anticoagulant powder 504 within the open cell foam material 502. In other embodiments, the open cell foam material 502 may contain other dry substances. The effective mixing is achieved by passing the blood sample through the open cell foam material 502 having the dry anticoagulant powder 504 distributed throughout its microstructure.

Figure 13:
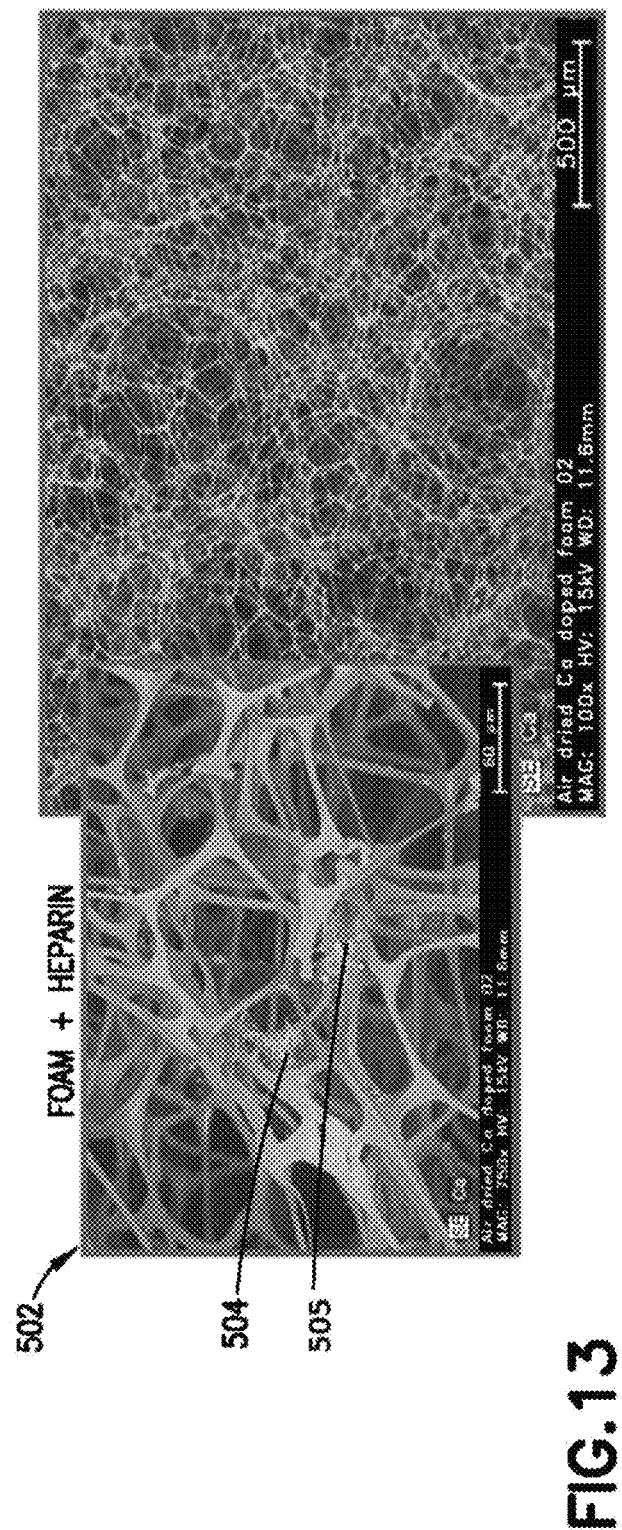
FIG. 13 is a microscopic view of the microstructure of an open cell foam material having a dry anticoagulant powder distributed throughout its microstructure in accordance with an embodiment of the present invention.
Figure 14:
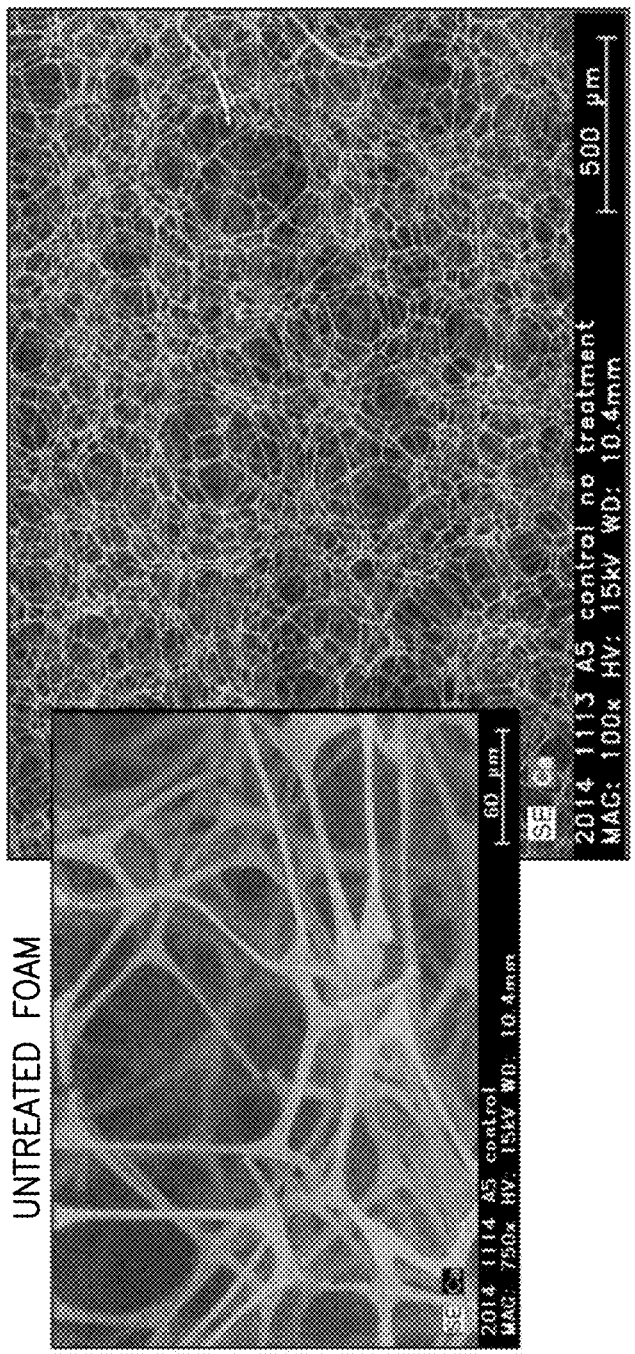
FIG. 14 is a microscopic view of the microstructure of an untreated foam material.
Figure 15:
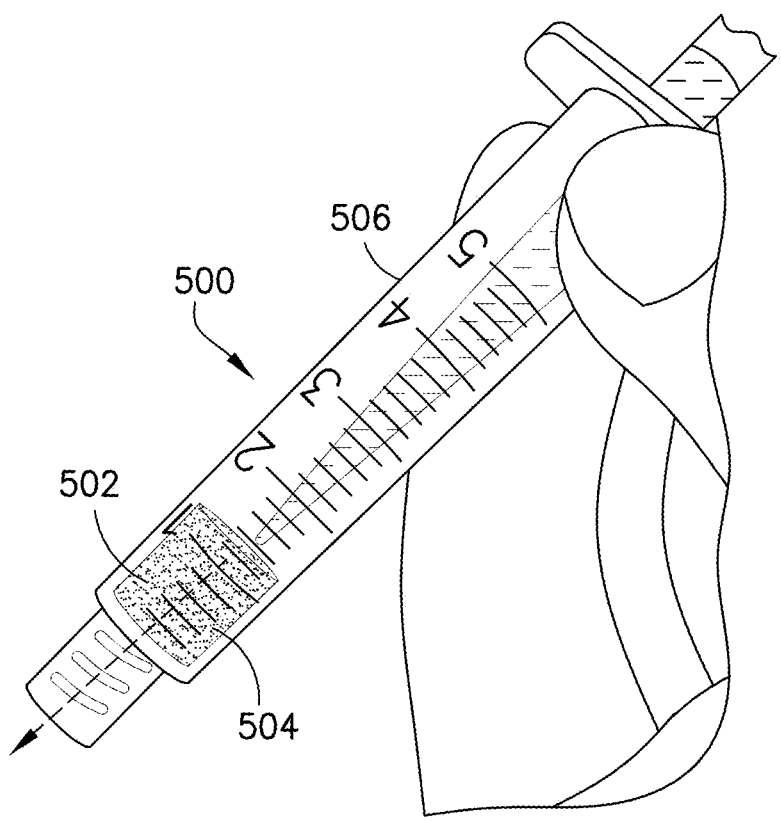
FIG. 15 is a perspective view of a syringe assembly in accordance with an embodiment of the present invention.
Figure 16:
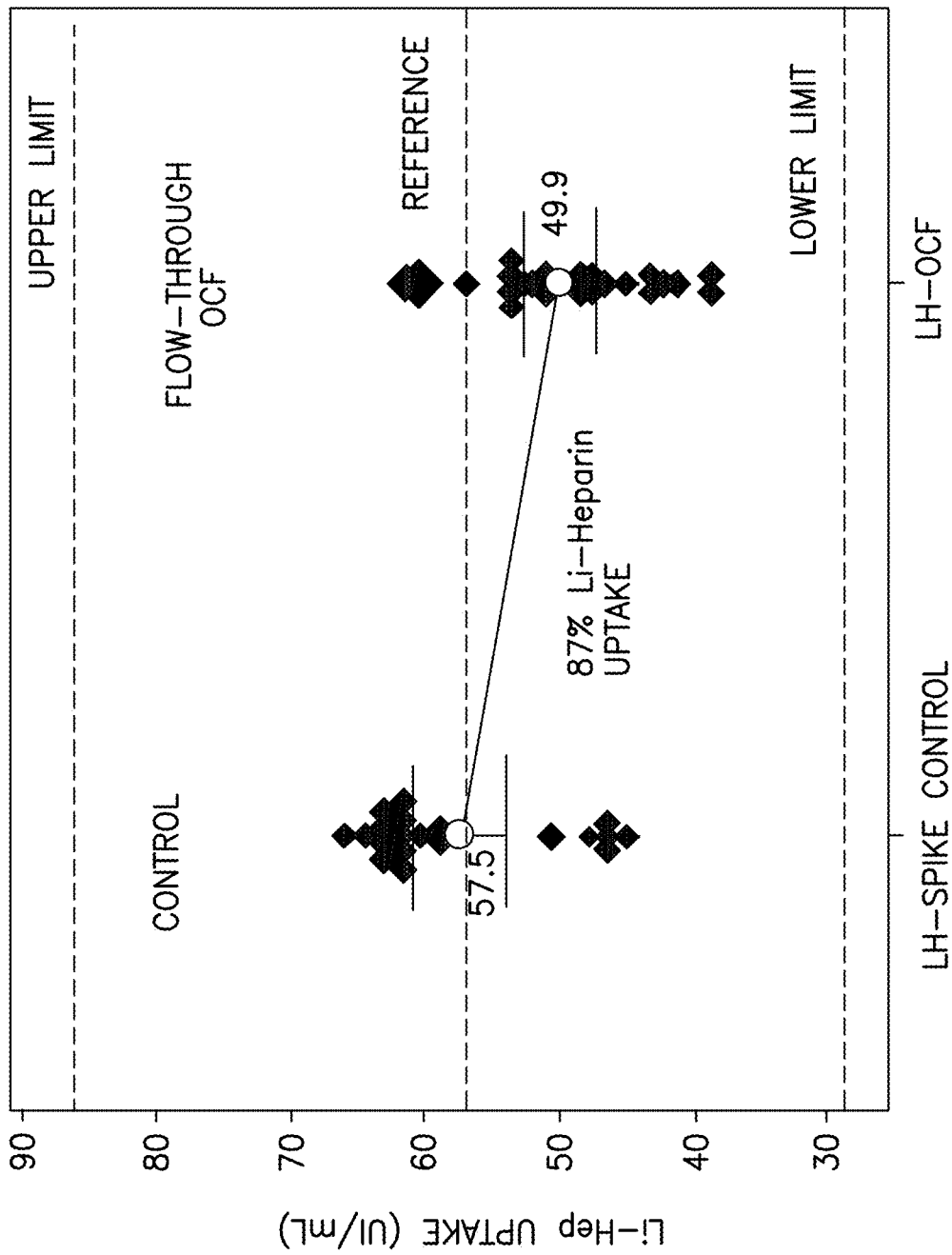
FIG. 16 is a graph demonstrating the anticoagulant uptake by a blood sample flowing through an open cell foam material having a dry anticoagulant powder distributed throughout its microstructure in accordance with an embodiment of the present invention.
Figure 18:
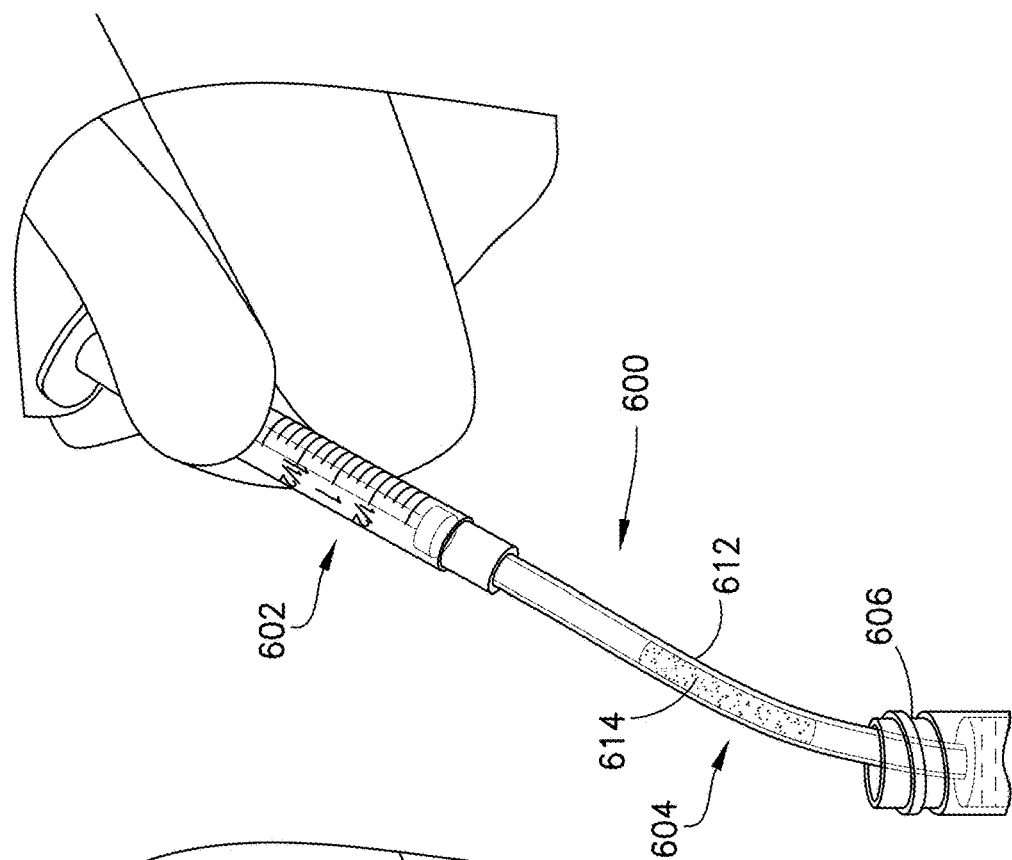
FIG. 18 is a perspective view of a blood transfer system in accordance with an embodiment of the present invention.
Figure 17:
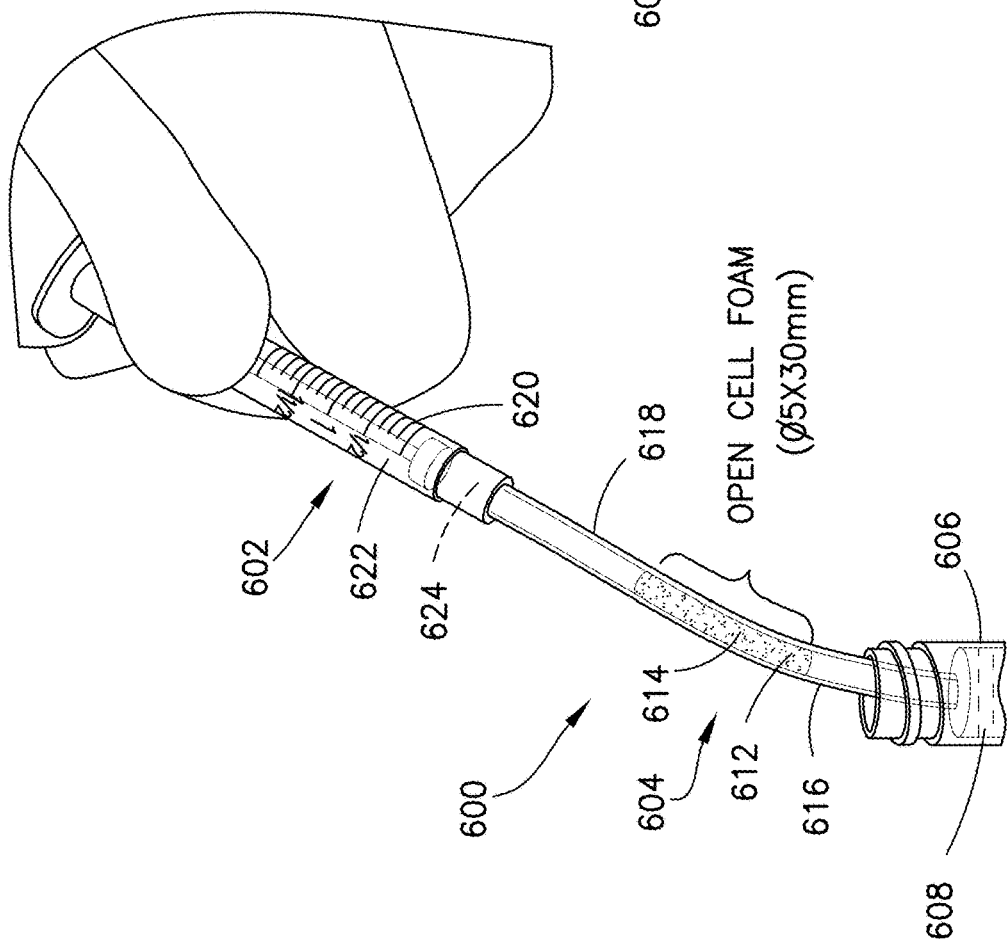
FIG. 17 is a perspective view of a blood transfer system in accordance with an embodiment of the present invention.
Figure 19:
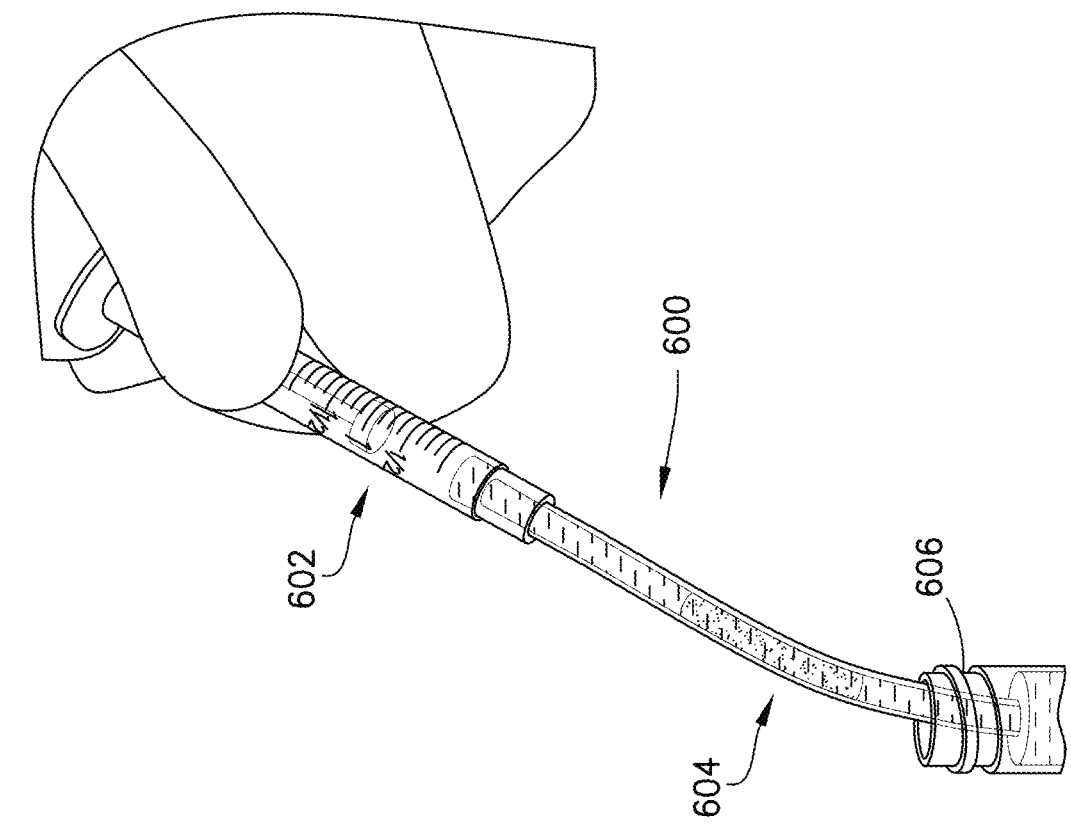
FIG. 19 is a perspective view of a blood transfer system in accordance with an embodiment of the present invention.
Figure 20:
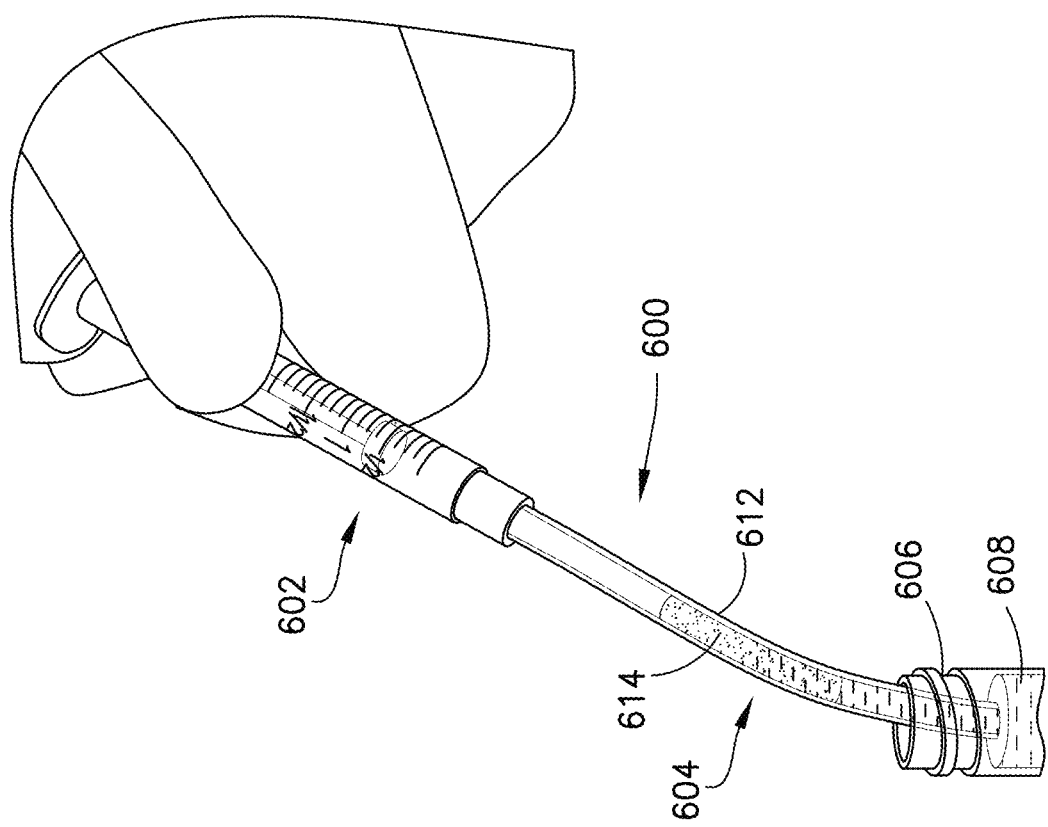
FIG. 20 is a perspective view of a blood transfer system in accordance with an embodiment of the present invention.

Referring to FIG. 13, a view of the microstructure of the open cell foam material 502 having a dry anticoagulant powder 504 distributed throughout its microstructure is illustrated. Referring to FIG. 14, a view of the microstructure of an untreated foam material 502 is illustrated. Referring to FIG. 16, a graph is illustrated demonstrating the anticoagulant uptake by a blood sample flowing through an open cell foam material having a dry anticoagulant powder distributed throughout its microstructure.

FIGS. 17-20 illustrate an exemplary embodiment of a specimen mixing and transfer system of the present disclosure. Referring to FIGS. 17-20, in one embodiment, a blood transfer system 600 includes a syringe assembly 602, a line 604, and a container 606. In one embodiment, the container 606 contains blood 608.

In one embodiment, the line 604 includes an open cell foam material 612 having a dry anticoagulant powder 614 therein. The anticoagulant can be loaded into the open cell foam material 612 having pores, as described above. The open cell foam material 612 is disposed within the line 604. The line 604 includes a first end 616 and a second end 618.

In one embodiment, the syringe assembly 602 includes a syringe barrel 620 and a sidewall 622 defining an interior 624. Referring to FIGS. 17-20, the line 604 is adapted to place the syringe assembly 602 and the container 606 in fluid communication. For example, the first end 616 of the line 604 can be in fluid communication with the contents of the container 606, and the second end 618 of the line 604 can be in fluid communication with the syringe assembly 602.

The open cell foam material 612 is placed in the line 604 for mixing and stabilizing blood. In one embodiment, the blood 608 is transferred from the container 606 to the syringe barrel 620 via the line 604. For example, a blood sample, e.g., blood 608, passes through the line 604 with the open cell foam material 612 embedded inside the line 604 as the blood gets collected into the syringe barrel 620. In this manner, the blood 608 is stabilized before entering the syringe barrel 620. After the stabilized blood 608 is contained within the syringe barrel 620, the stabilized blood 608 can then be dispensed for analysis.

In one embodiment, the line 604 acts as a flow-through chamber for the effective mixing of a blood sample with the dry anticoagulant powder 614 within the open cell foam material 612. In other embodiments, the open cell foam material 612 may contain other dry substances. The effective mixing is achieved by passing the blood sample through the open cell foam material 612 having the dry anticoagulant powder 614 distributed throughout its microstructure.

The present disclosure provides a material that includes pores and has a dry anticoagulant powder within the pores of the material, as described above. In one embodiment, the material is a sponge material. In other embodiments, the material is an open cell foam. In one embodiment, the open cell foam is treated with an anticoagulant, as described in detail above, to form a dry anticoagulant powder finely distributed throughout the pores of the material.

The present disclosure provides different applications and embodiments of the material. For example, in one embodiment, a specimen mixing and transfer device of the present disclosure is adapted to receive a sample. The specimen mixing and transfer device includes a housing, a material including pores that is disposed within the housing, and a dry anticoagulant powder within the pores of the material. In one embodiment, the material is a sponge material. In other embodiments, the material is an open cell foam. In one embodiment, the open cell foam is treated with an anticoagulant to form a dry anticoagulant powder finely distributed throughout the pores of the material. A blood sample may be received within the specimen mixing and transfer device. The blood sample is exposed to and mixes with the anticoagulant powder while passing through the material.

A specimen mixing and transfer device of the present disclosure offers uniform and passive blood mixing with an anticoagulant under flow-through conditions. A specimen mixing and transfer device of the present disclosure could catch blood clots or other contaminants within the microstructure of the material and prevent them from being dispensed into a diagnostic sample port. A specimen mixing and transfer device of the present disclosure enables a simple, low-cost design for passive flow-through blood stabilization. A specimen mixing and transfer device of the present disclosure enables precisely controlled loading of an anticoagulant into the material by soaking it with an anticoagulant and water solution and then drying the material to form a finely distributed dry anticoagulant powder throughout the pores of the material.

A specimen mixing and transfer device of the present disclosure may provide an effective passive blood mixing solution for applications wherein blood flows through a line. Such a specimen mixing and transfer device is useful for small blood volumes, e.g., less than 50 µL, or less than 500 µL, and/or where inertial, e.g., gravity based, forces are ineffective for bulk manual mixing by flipping back and forth a blood collection container such as is required for vacuum tubes.

In other embodiments of the present disclosure, the material can be utilized with a specimen mixing and transfer system or a syringe assembly, as described above.

While this disclosure has been described as having exemplary designs, the present disclosure can be further modified within the spirit and scope of this disclosure. This application is therefore intended to cover any variations, uses, or adaptations, of the disclosure using its general principles. Further, this application is intended to cover such departures from the present disclosure as come within known or customary practice in the art to which this disclosure pertains and which fall within the limits of the appended claims.

What is claimed is:

1. A specimen mixing and transfer device adapted to receive a sample, comprising:
   a housing having a first end including an inlet, a second end including an outlet, and a sidewall extending therebetween;
   a material including pores and disposed within the housing;
   a dry anticoagulant powder within the pores of the material;
   a mixing chamber formed integral with the housing, the material disposed within the mixing chamber; and
   a dispensing chamber in fluid communication with the mixing chamber and formed integral with the housing, the dispensing chamber configured to hold the sample until it is desired to transfer the sample from the dispensing chamber, the dispensing chamber positioned between the mixing chamber and the outlet, the dispensing chamber positioned adjacent the outlet of the housing;
   wherein the material is a melamine open cell foam.

2. The specimen mixing and transfer device of claim 1, wherein the housing is adapted to receive the blood sample therein via the first end.

3. The specimen mixing and transfer device of claim 2, wherein, with the blood sample received within the housing, the blood sample passes through the material thereby effectively mixing the blood sample with the dry anticoagulant powder.

4. The specimen mixing and transfer device of claim 3, wherein the blood sample dissolves and mixes with the dry anticoagulant powder while passing through the material.

5. The specimen mixing and transfer device of claim 1, wherein the housing further comprises an inlet channel in fluid communication with the inlet and the mixing chamber and an outlet channel in fluid communication with the mixing chamber and the outlet.

6. The specimen mixing and transfer device of claim 5, wherein the dispensing chamber is provided between the mixing chamber and the outlet.

7. A specimen mixing and transfer device adapted to receive a sample, comprising:
   a housing having a first end including an inlet, a second end including an outlet, and a sidewall extending therebetween;
   a dry anticoagulant powder disposed within the housing;
   a mixing element disposed within the housing, wherein the mixing element comprises at least one rigid post;
   a mixing chamber formed integral with the housing, the dry anticoagulant powder disposed within the mixing chamber; and
   a dispensing chamber in fluid communication with the mixing chamber and formed integral with the housing, the dispensing chamber configured to hold the sample until it is desired to transfer the sample from the specimen mixing and transfer device, the dispensing chamber positioned between the mixing chamber and the outlet, the dispensing chamber positioned adjacent the outlet of the housing;
   wherein the housing comprises both the mixing chamber and the dispensing chamber, and
   wherein the sample is a blood sample.

8. The specimen mixing and transfer device of claim 7, wherein the housing is adapted to receive the blood sample therein via the first end.

9. The specimen mixing and transfer device of claim 8, wherein, with the blood sample received within the housing, the mixing element interferes with a flow of the blood sample to promote mixing of the blood sample with the dry anticoagulant powder.

10. The specimen mixing and transfer device of claim 7, wherein the mixing element comprises a plurality of posts.

11. The specimen mixing and transfer device of claim 7, wherein the housing further comprises an inlet channel in fluid communication with the inlet and the mixing chamber and an outlet channel in fluid communication with the mixing chamber and the outlet.

12. The specimen mixing and transfer device of claim 11, wherein the dispensing chamber is provided between the mixing chamber and the outlet.

13. The specimen mixing and transfer device of claim 11, wherein the housing further comprises two diverted flow channels between the inlet channel and the outlet channel.

* * * * *

UNITED STATES PATENT AND TRADEMARK OFFICE
CERTIFICATE OF CORRECTION

| | | |
|---|---|---|
| PATENT NO. | : 11,298,061 B2 | Page 1 of 1 |
| APPLICATION NO. | : 14/861167 | |
| DATED | : April 12, 2022 | |
| INVENTOR(S) | : Ivosevic et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 372 days.

Signed and Sealed this
Fifteenth Day of November, 2022

Katherine Kelly Vidal
*Director of the United States Patent and Trademark Office*